United States Patent
Kumamoto et al.

(10) Patent No.: US 7,067,254 B2
(45) Date of Patent: Jun. 27, 2006

(54) DIAGNOSIS AND TREATMENT OF INFLAMMATION AND HYPERACTIVE IMMUNE CONDITIONS

(75) Inventors: Tadashi Kumamoto, Mie (JP); Norikatsu Mizumoto, Irving, TX (US); Akira Takashima, Coppell, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 633 days.

(21) Appl. No.: 10/074,220

(22) Filed: Feb. 12, 2002

(65) Prior Publication Data

US 2003/0087247 A1    May 8, 2003

Related U.S. Application Data

(60) Provisional application No. 60/334,618, filed on Nov. 1, 2001, provisional application No. 60/273,212, filed on Mar. 1, 2001.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .......... 435/6; 435/91.2; 536/23.5; 536/24.31; 536/24.33

(58) Field of Classification Search .......... 435/6, 435/91.2
See application file for complete search history.

(56) References Cited

FOREIGN PATENT DOCUMENTS

WO    WO 98/28437    7/1998

OTHER PUBLICATIONS

Mizumoto et al. Journal of Invest. Dermat. vol. 121, No. 5, Nov. 2003 pp. 1066-1072.*
Alberts et al.(1998 www.essentialcellbiology.com).*
Offord et al. Carcinogenesis vol. 14 No. 12 pp. 2447-2455, 1993.*
Alberts et al. Molecular biology of the Cell, 3rd edition 1994.*
Middleton, MC The Journal of Investigative Dermatology, 79:163-166, 1982.*
Bodin et al. (Inflammatory Research 47 (1998) 351-354.*
Berchtold et al., "Human monocyte derived dendritic cells express functional P2X and P2Y receptors as well as ecto-nucleotidases," *FEBS Lett.*, 458:424-428, 1999.
Betto, et al., "Ecto-ATPase activity of alpha-sarcoglycan (adhalin)" *J. Biol. Chem.*, 274: 7907-7912, 1999.
Biederbick, et al., "A human intracellular apyrase-like protein, LALP70, localizes to lysosomal/autophagic vacuoles," *J. Cell Sci.*, 112: 2473-2484, 1999.

Chadwick and Frischauf, "The CD39-like gene family: identification of three new human members (CD39L2, CD39L3, and CD39L4), their murine homologues, and a member of the gene family from Drosophila melanogaster," *Genomics*, 50:357-367, 1998.
Coutinho-Silva et al., "P2Z/P2X7 receptor-dependent apoptosis of dendritic cells," *Am. J. Physiol.* 276:C1139-C1147, 1999.
Di Virgilio, et al., "Nucleotide receptors: an emerging family of regulatory molecules in blood cells," *Blood*, 97: 587-600, 2001.
Dumbrowski et al., "Ecto-ATPase; an activation marker necessary for effector cell function," *Immunol Rev.*, 161:111-118, 1998.
Effendy, et al., "Epidermal cytokines in murine cutaneous irritant responses," *J. Appl. Toxicol.*, 20: 335-341, 2000.
Enjyoji, et al. "Targeted disruption of cd39/ATP diphosphohydrolase results in disordered hemostasis and thromboregulation," *Nat. Med.*, 5:1010-1017, 1999.
Ferrari, et al. "The P2 purinergic receptors of human dendritic cells: identification and coupling to cytokine release," *FASEB J.*, 14: 2466-2476, 2000.
Filippini, et al., "Extracellular ATP in T-lymphocyte activation: possible role in effector functions," *Proc. Natl. Acad. Sci. U. S. A*, 87: 8267-8271, 1990.
Girolomoni et al., "Epidermal Langerhans cells are resistant to the permeabilizing effects of extracellular ATP: in vitro evidence supporting a protective role of membrane ATPase," *J. Invest Dermatol.*, 100:282-287, 1993.

(Continued)

Primary Examiner—Jeffrey Fredman
Assistant Examiner—Sally Sakelaris
(74) Attorney, Agent, or Firm—Fulbright & Jaworski

(57) ABSTRACT

Ecto-NTPDase function on Langerhans cells is demonstrated to counteract the nucleotide inflammatory response caused by certain types of chemical irritants. The present invention takes advantage of this observation by, first, providing methods for screening of chemicals for irritant potential based on their ability to induce nucleotide release from keratinocytes. Second, methods are provided for the prevention and treatment of inflammation using NTPDase protein or gene therapy. And third, there also are provided methods for screening candidate compounds for NTPDase modulatory activity, thereby identifying possible pro- and anti-inflammatory agents. Additionally, the role of NTPDases and P2 receptors in hyperactive immune conditions such as autoimmune diseases and allergic reactions such as allergic contact dermatitis has been demonstrated. Therefore, the invention also provides methods for the prevention and treatment of hyperactive immune conditions by using NTPDase inhibitors and/or P2 receptor inhibitors. Further provided are methods for screening candidate compounds for modulatory activity of NTPDase-mediated immune conditions, thereby identifying other possible immunotherapeutic agents.

11 Claims, 11 Drawing Sheets

OTHER PUBLICATIONS

Heine, et al., "Functional characterization of rat ecto-ATPase and ecto-ATP diphosphohydrolase after heterologous expression in CHO cells," *Eur J Biochem.*, 262(1):102-107, 1999.

Imai, et al., "CD39 modulates IL-1 release from activated endothelial cells," *Biochem. Biophys. Res. Commun.*, 270: 272-278, 2000.

Knowles and Nagy, "Inhibition of an ecto-ATP-diphosphohydrolase by azide," *Eur. J. Biochem.*, 262:349-357, 1999.

Liu et al. "Expression and a role of functionally coupled P2Y receptors in human dendritic cells," *FEBS Lett.*, 445:402-408, 1999.

Marriott, et al., "Extracellular uridine nucleotides initiate cytokine production by murine dendritic cells," *Cell. Immunol.*, 195:147-156, 1999.

Matsue et al., "Induction of antigen-specific immunosuppression by CD95L cDNA-transfected "killer" dendritic cells," *Nature Med.*, 5:930-937, 1999.

Matsue, et al., "Keratinocyte-derived IL-7 serves as a growth factor for dendritic epidermal T-cells in mice," *J. Immunol.*, 151:6012-6019, 1993.

Mummert, et al., "Development of a peptide inhibitor or hyaluronan-mediated leukocyte trafficking," *J. Exp. Med.*, 192:769-779, 2000.

Mutini et al., "Mouse dendritic cells express the $P2X_7$ purinergic receptor: characterization and possible participation in antigen presentation," *J. Immunol.*, 163:1958-1965, 1999.

Nihei, et al., "Pharmacologic properties of $P_{2Z}$/$P2X_7$ receptor characterized in murine dendritic cells: role on the induction of apoptosis," *Blood*, 96: 996-1005, 2000.

Ralevic and Burnstock, "Receptors for purines and pyrimidines," *Pharmacol. Rev.* 50:413-492, 1998.

Sellers, et al., "Adenosine nucleotides acting at the human P2Y1 receptor stimulate mitogen-activated protein kinases and induce apoptosis," *J. Biol. Chem.*, 276: 16379-16390, 2001.

Sevigny, et al., "Identification and characterization of a novel hepatic canalicular ATP diphosphohydrolase," *J. Biol. Chem.*, 275: 5640-5647, 2000.

Wang, and Guidotti, "Golgi localization and functional expression of human uridine diphosphatase," *J. Biol. Chem.*, 273: 11392-11399, 1998.

Warny, et al., "P2Y(6) nucleotide receptor mediates monocyte interleukin-8 production in response to UDP or lipopolysaccharide," *J. Biol. Chem.*, 276: 26051-26056, 2001.

Williams and Jarvis, "Purinergic and pyrimidinergic receptors as potential drug targets," *Biochem. Pharmacol.*, 59: 1173-1185, 2000.

Xu, et al., "Successive generation of antigen-presenting, dendritic cell lines from murine epidermis," *J. Immunol.*, 154:2697-2705, 1995.

Zhong and Guidotti, "A yeast Golgi E-type ATPase with an unusual membrane topology," *J.Biol.Chem.*, 274:32704-32711, 1999.

Ziganshina, et al., "Acute paw oedema formation induced by ATP: re-evaluation of the mechanisms involved," *Inflamm. Res.*, 45: 96-102, 1996.

Zinchuk et al., "Ecto-ATPase activity in cerebellum: implication to the function of synaptic transmission," *Brain Res.* 815:111-115, 1999.

Homolya et al., "Cell to cell communication in response to mechanical stress via bilateral release of ATP and UTP in polarized epithelia," *J. Cell Biol.*, 150:1349-1359, 2000.

Kaplan et al., "Extracellular nucleotides act through $P_{2U}$ purinoceptors to elevate [$Ca^{2+}$] and enhance basic fibroblast growth factor-induced proliferation in sheep chondrocytes," *Endocrinology*, 137:4757-4766, 1996.

Kaplan et al., "Extracellular nucleotides potentiate the cytosolic $Ca^{2+}$, but not cyclic adenosine 3', 5'-monophosphate response to parathyroid hormone in rat osteoblastic cells," *Endocrinology*, 136:1674-1685, 1995.

Narravula et al., "Regulation of endothelial CD73 by adenosine: paracrine pathway for enhanced endothelial barrier function," *J. of Immunology*, 165:5262-5268, 2000.

* cited by examiner

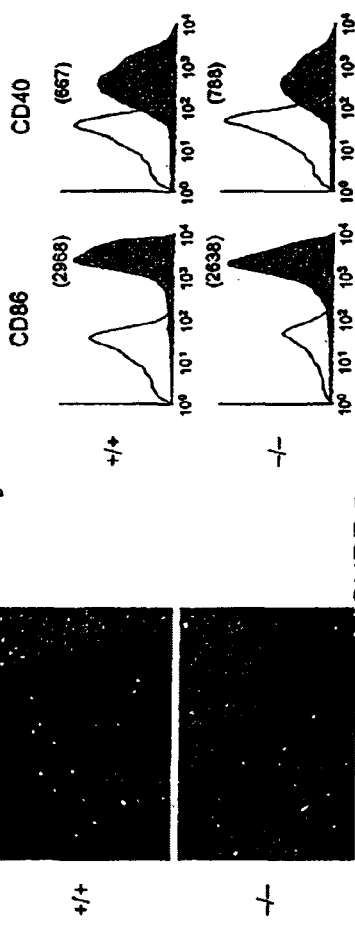
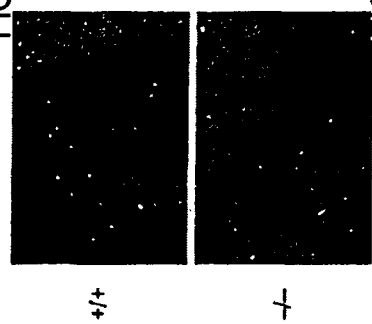
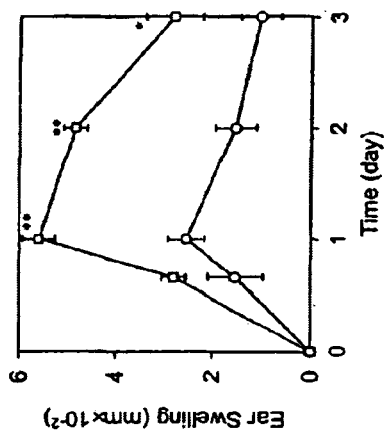
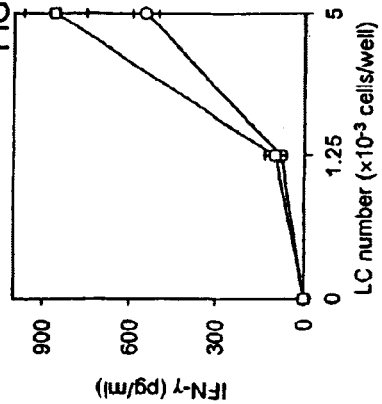
FIGURE 5e
FIGURE 5f
FIGURE 5g
FIGURE 5h

DIAGNOSIS AND TREATMENT OF INFLAMMATION AND HYPERACTIVE IMMUNE CONDITIONS

The present application claims priority to co-pending U.S. Provisional Patent Applications Ser. No. 60/273,212 filed Mar. 1, 2001 and 60/334,618 filed Nov. 1, 2001. The entire text of the above-referenced disclosures are specifically incorporated by reference herein without disclaimer.

The government owns rights in the present invention pursuant to grant numbers R01 AR43777 from the National Institutes of Health.

BACKGROUND OF THE INVENTION

I. Field of the Invention

The present invention relates to the fields of cell biology and biochemistry generally, and more specifically to the use nucleotide release as a measure of inflammatory action of a chemical. In addition, the present invention relates to the prevention and treatment of inflammation using nucleoside triphosphate diphosphohydrolase (NTPDase) activity, and includes protein-based and gene-based therapies. The invention also provides methods for screening candidate compounds for NTPDase modulatory activity. Furthermore, the invention provides methods for treating and/or preventing hyperactive immune disorders using NTPDase inhibitors or P2-receptor inhibitors. Methods for screening for modulators of NTPDase-mediated immune responses are also provided.

II. Brief Description of the Prior Art

Irritant contact dermatitis, the most frequent type of skin inflammation, results from contact with a substance that chemically damages the skin. As new chemicals are constantly being developed for use in many commercial products, including cosmetics, drugs, clothes, diapers, paints, soaps, shampoos, cleaning solutions, detergents, adhesives, food and food packaging, contraceptives, household cleaners, automobile interiors and parts, recycled paper, garden chemicals and other household products, cases of irritant contact dermatitis are on an exponential rise. Accidental, occupational or consumer-based exposure to such products can result in acute or chronic irritant contact dermatitis—the most common occupational health problem, and the most common skin disorder, in the United States.

Signs and symptoms of contact dermatitis can include skin inflammation characterized by redness, bumps, blisters, scaling, swelling, oozing, crusting, itching, and pain. These symptoms often occur at the site of contact, which is frequently the hands, arms, or legs, or face, but can occur elsewhere on the skin as well.

In spite of the rise in the number of cases of irritant contact dermatitis, efforts to develop assays which accurately predict the irritant potential of various chemicals have not been successful. Thus, there remains a need to develop accurate and sensitive assays for predicting irritant potential, as well as methods for the treatment thereof.

In addition to irritant contact dermatitis, diseases that are caused by hyperactivity of the immune system also are of concern. These diseases include a spectrum of allergic and autoimmune conditions that are associated with immunologically-mediated damage to the host tissue. Allergic contact dermatitis is another form of dermatitis which is one of the leading occupational hazards in the United States. Other allergic conditions include atopic dermatitis, hay fever, asthma and the like. Examples of autoimmune diseases include multiple sclerosis, rheumatoid arthritis, Crohn's disease, systemic lupus eryrthmatosus (SLE), etc. These diseases afflict many individuals and cause significant morbidity and mortality. Treatments for autoimmune diseases generally include immune suppression. Unfortunately, generalized immune suppression often results in increased incidence of infections and malignancies. Therefore, treatment of patients with an immunological disorder is at the cost of placing the patient at a risk of developing other, possibly life threatening, diseases.

What is required in the art is the identification of molecular targets of the immune system that play a role in hyperactive immune conditions and the development of screening methods to identify agents that can modulate these molecular targets. These agents can then be used therapeutically to treat/prevent immune hyperactivity.

SUMMARY OF THE INVENTION

The present invention overcomes these and other defects in the art and demonstrates that an ecto-NTPDase function on dendritic Langerhans cells is required to counteract nucleotide mediated inflammatory response caused by certain types of chemical irritants. The invention provides methods for screening of chemicals for irritant potential based on their ability to induce nucleotide release from cells. The invention also provides methods for the prevention and treatment of inflammation using NTPDase protein-based and/or gene-based therapies. In addition, the invention also provides methods for screening candidate compounds for NTPDase modulatory activity, thereby identifying pro- and anti-inflammatory agents.

Therefore, provided is a method for predicting the irritant potential of a candidate substance comprising: (a) providing a mammalian cell that releases a nucleotide in response to an inflammatory agent; (b) culturing the cell with a candidate substance; and (c) determining nucleotide release from the cell, wherein an increase in nucleotide release from the cell, as compared to nucleotide release in the absence of the candidate substance, indicates that the candidate substance is an irritant.

In one embodiment of this method, the cell is a fibroblast. In another embodiment, the cell is a keratinocyte. In some specific embodiments, the keratinocyte is a human keratinocyte. In other specific embodiments, the keratinocyte is a mouse keratinocyte. In yet another embodiment of the method, the cell is a PAM 212 cell. The skilled artisan will recognize that the cell can be any cell that is capable of releasing a nucleotide in response to an inflammatory agent or to a chemical irritant and that the practice of this invention is not limited to the examples described above.

The nucleotide can be a nucleotide triphosphate (NTP), a nucleotide diphosphate (NDP), or a nucleotide monophosphate (NMP). In one embodiment, the nucleotide is ATP and/or ADP and/or AMP. In another embodiment, the nucleotide is UTP and/or UDP and/or UMP. In yet another embodiment, the nucleotide is CTP and/or CDP and/or CMP. In still other embodiments, the nucleotide is GTP and/or GDP and/or GMP. In yet other embodiments, the nucleotide is TTP and/or TDP and/or TMP.

In one embodiment, determining nucleotide release from the cell comprises measuring nucleotide concentration in the cell culture medium. Thus, for example, the ATP and/or ADP and/or AMP release can be measured by measuring the ATP and/or ADP and/or AMP concentration in the cell medium; the UTP and/or UDP and/or UMP release can be measured by measuring the UTP and/or UDP and/or UMP concentration in the cell medium, and likewise for other nucleotides.

In another embodiment, measuring nucleotide concentration comprises an enzymatic assay. The enzymatic assay can be a luciferin-luciferase assay and/or a pyruvate kinase assay. In an alternative embodiment, measuring nucleotide concentration comprises chromatographic measurements and includes any chromatographic procedure including, for example, thin layer chromatography and liquid chromatography.

In some aspects, the candidate substance with irritant potential is a naturally-occurring compound. In other aspects the candidate substance is a man-made compound.

In one embodiment the method further comprises measuring nucleotide release from the cell in the absence of the candidate substance as a control. The method described can also further comprise another control which comprises: (i) contacting the cell with a known irritant; and (ii) measuring nucleotide release from the cell.

The invention also provides a method for preventing an inflammatory response in a subject comprising administering to the subject a composition comprising a NTPDase. The NTPDase can be an ATPase and/or an ADPase; a UTPase and/or a UDPase; a CTPase and/or a CDPase; a GTPase and/or a GDPase; or a TTPase and/or a TDPase. In some embodiments of this method, the NTPDase is selected from the group consisting of CD39, CD39L1, CD39L2, CD39L3, CD39L4, Golgi-associated ecto-ATPase and ecto-uridine diphosphatase (UDPase), lysosomal ecto-apryase LALP70, hepatic canalicular ecto-apyrase, (α-sarcoglycan and potato apyrase.

In other embodiments of this method, the inflammatory response is chemical skin irritation, and the NTPDase is applied as a topical formulation. In yet other aspects, the NTPDase is applied as an oral, intranasal, intratracheal, intraesophageal, intrabronchial, intra-vaginal or rectal formulation.

The inflammatory response can be caused by a pro-inflammatory leukocyte or by a soluble pro-inflammatory factor. In one aspect of this embodiment, the soluble pro-inflammatory factor is a cytokine, a prostaglandin, or a histamine.

The invention also provides methods for treating an inflammatory response in a subject which comprise administering to the subject a composition comprising a NTPDase.

The invention also provides a method for preventing an inflammatory response in a subject comprising administering to the subject an expression construct comprising a DNA segment encoding a NTPDase under the control of a promoter active in cells of the subject. In one embodiment of the method, the expression construct is a viral expression construct. In a specific embodiment, the viral expression construct is selected from the group consisting of a retrovirus, an adenovirus, an adeno-associated virus, a herpesvirus, a polyoma virus, and a vaccinia virus.

In another embodiment, the expression construct is a non-viral expression construct. In one aspect, the non-viral expression construct can be administered as a naked DNA. In another aspect, the non-viral expression construct is administered in a liposomal formulation.

In one embodiment of this method, the NTPDase encoded by the expression construct is selected from the group consisting of CD39, CD39L1, CD39L2, CD39L3, CD39L4, Golgi-associated ecto-ATPase and ecto-uridine diphosphatase (UDPase), lysosomal ecto-apryase LALP70, hepatic canalicular ecto-apyrase, α-sarcoglycan and potato apyrase.

In another embodiment of this method, the inflammatory response is chemical skin irritation, and the NTPDase is applied as a topical formulation. In specific aspects the inflammatory response is mucosal irritation, and the NTPDase is applied as an oral, intranasal, intratracheal, intraesophageal, intrabronchial, intra-vaginal or rectal formulation. In other specific aspects, the inflammatory response is caused by a pro-inflammatory leukocyte. In yet other aspects, the inflammatory response is caused by a soluble pro-inflammatory factor, such as a cytokine, a prostaglandin, or a histamine.

The invention also provides a method for treating an inflammatory response in a subject comprising administering to the subject an expression construct comprising a DNA segment encoding a NTPDase under the control of a promoter active in cells of the subject.

The invention further provides methods of screening for modulators of inflammation comprising: (a) providing a cell that expresses a NTPDase; (b) contacting the cell with a candidate substance; and (c) determining the effect of the candidate substance on the NTPDase expression in the cell, wherein a change in the expression of a NTPDase in the cell, as compared to NTPDase expression in the absence of the candidate substance, indicates that the candidate substance is a modulator of a NTPDase expression, and therefore a modulator of inflammation. In one embodiment, the modulator is an inhibitor of inflammation. In another embodiment, the modulator is a promoter of inflammation.

In one aspect of this method the cell is a dendritic cell. In specific aspects, the dendritic cell is a Langerhans cell or cell line and is exemplified by the XS52 or the XS106 cells.

In one embodiment, the cell comprises an expression construct comprising a DNA segment encoding the NTPDase under the control of a promoter active in the cell. In one aspect, the determining comprises measuring NTPDase levels in the cell. In another aspect, the measuring comprises measuring a NTPDase on the surface of the cell. In yet another aspect, the determining comprises measuring the NTPDase activity of the cell.

The NTPDase activity can be measured by methods that measure the surface enzyme activity. Concentrations of nucleotides, released as a result of the surface enzyme activity, can be measured to measure the NTPDase activity. The NTPDase activity can also be measured by methods comprising using an enzyme linked immunoassay using an enzyme-labeled anti-NTPDase antibody. In another aspect of the method, fluorescent activated cell sorting of cells using a fluorescent-labeled anti-NTPDase antibody is used. In yet another aspect, the determining comprises measuring NTPDase mRNA levels in the cell. In such embodiments, the method can comprise Northern blotting and/or quantitative RT-PCR.

In specific examples of this embodiment, the NTPDase can be a ATPase and/or ADPase; an UTPase and/or an UDPase; etc.

The invention additionally provides a method of screening for modulators of inflammation comprising: (a) providing a cell that comprises an expression construct comprising a DNA segment encoding a screenable marker under the control of a promoter for a NTPDase; (b) contacting the cell with a candidate substance; and (c) determining the effect of the candidate substance on expression of the selectable marker, wherein a change in the expression of the selectable marker, as compared to selectable marker expression in the absence of the candidate substance, indicates that the candidate substance is a modulator of NTPDase promoter expression, and therefore a modulator of inflammation. The modulator can be either an inhibitor of inflammation or a promoter of inflammation.

In specific aspects of this method, the NTPDase can be selected from the group consisting of CD39, CD39L1, CD39L2, CD39L3, CD39L4, Golgi-associated ecto-ATPase and ecto-uridine diphosphatase (UDPase), lysosomal ecto-apryase LALP70, hepatic canalicular ecto-apyrase, α-sarcoglycan and potato apyrase.

In one embodiment, the screenable marker is an enzyme and determining comprises measuring enzyme activity. Examples of such enzymes include urease, alkaline phosphatase or peroxidase for which colorimetric indicator substrates can be employed to provide a detection means visible to the human eye or by spectroscopy.

In one embodiment, the invention also provides methods of screening for a modulator of inflammation comprising: (a) providing a cell that expresses a membrane bound NTPDase, or ecto-NTPDase in a culture solution comprising a nucleotide; (b) contacting the cell with a candidate substance; and (c) determining the effect of the candidate substance on NTP, NDP and/or NMP levels in the culture solution, wherein a change in the NTP, NDP and/or NMP levels in the culture solution, as compared to NTP, NDP and/or NMP levels in the absence of the candidate substance, indicates that the candidate substance is a modulator of NTPDase activity, and therefore a modulator of inflammation.

In one aspect of this method, the cell expresses an NTPDase. In another aspect the cell expresses an NTPDase. The modulator can be either an inhibitor of inflammation or a promoter of inflammation.

In some aspects, the NMP levels, such as AMP, UMP, GMP, CMP and/or TMP, are detected by chromatographic methods, including thin layer chromatography, liquid chromatography, high-performance liquid chromatography and cation-exchange chromatography.

The present inventors have also identified that NTPDases are involved in certain hyperactive immune responses such as autoimmune conditions and allergic reactions. Therefore, the present invention also provides methods for treating a hyperactive immune response in a subject comprising administering to the subject a composition comprising a NTPDase inhibitor.

The NTPDase inhibitor may be an ATPase inhibitor and/or ADPase inhibitor, an UTPase inhibitor and/or UDPase inhibitor, a CTPase inhibitor and/or CDPase inhibitor, a TTPase inhibitor and/or TDPase inhibitor, or a GTPase inhibitor and/or GDPase inhibitor.

In one embodiment of the invention, the NTPDase inhibitor is an NTPDase antagonist, an anti-NTPDase antibody, an antisense oligonucleotide, or a chemical substance.

In one specific embodiment, the NTPDase antagonist is Azide, Evans Blue, Suramin, PPADS, DEPC, P-CMPS, P-HMB, NP-40, FSBA. Concentrations of the NTPDase antagonists are approximately in the range of 10–20 μM for Azide, 100 μM of Evans Blue, 100 μM of Suramin, 100 μM of PPADS, 1 mM of DEPC, 40 μM of P-CMPS, 40 μM of P-HMB, 10:1, w/w of NP-40, and 2 mM of FSBA.

In another specific embodiment of the invention, the anti-NTPDase antibody is an anti-ATPase and/or anti-ADPase antibody, an anti-UTPase and/or anti-UDPase antibody, a anti-CTPase and/or anti-CDPase antibody, a anti-TTPase and/or anti-TDPase antibody, or a anti-GTPase and/or anti-GDPase antibody.

In yet another specific embodiment of the invention, the antisense oligonucleotide comprises a nucleic acid that is complementary to a nucleic acid sequence encoding an ATPase and/or ADPase, an UTPase and/or UDPase, a CTPase and/or CDPase, a TTPase and/or TDPase, or a GTPase and/or GDPase, or a fragment thereof.

In one embodiment of the method, the NTPDase inhibitor is an inhibitor of CD39, CD39L1, CD39L2, CD39L3, CD39L4, Golgi-associated ecto-ATPase and ecto-uridine diphosphatase (UDPase), lysosomal ecto-apryase LALP70, hepatic canalicular ecto-apyrase, α-sarcoglycan or potato apyrase.

In one embodiment, the hyperactive immune response can be an allergic reaction and includes, but is not limited to conditions such as allergic contact dermatitis, atopic dermatitis, allergic rhinitis (hay fever), bronchial asthma, and the like.

In another embodiment, the hyperactive immune response is an autoimmune disease and is exemplified in non-limiting examples by Addison's disease, alopecia, ankylosing spondylitis, antiphospholipid syndrome, Behcet's disease, chronic fatigue syndrome, Crohn's disease, ulcerative colitis, diabetes, fibromyalgia, Goodpasture syndrome, Graves' disease, idiopathic thrombocytopenic purpura, lupus, Meniere's multiple sclerosis, myasthenia gravis, pemphigus vulgaris, primary biliary cirrhosis, psoriasis, rheumatoid arthritis, rheumatic fever, sarcoidosis, scleroderma, vasculitis, vitiligo, or Wegener's granulomatosis.

The NTPDase inhibitor may be administered by topical, oral, intranasal, intratracheal, intraesophageal, intrabronchial, intravenous, intraarterial, intramuscular, subcutaneous, intra-vaginal or rectal routes. The route of choice for administration will be decided on the nature and location of the hyperactive immune being treated.

The invention also provides methods for preventing a hyperactive immune response in a subject comprising administering to the subject a composition comprising a NTPDase inhibitor.

Additionally, methods for treating or preventing a hyperactive immune response in a subject comprising administering to the subject an expression construct comprising a DNA segment encoding a NTPDase inhibitor under the control of a promoter active in cells of the subject are provided.

In one embodiment of this method, the NTPDase inhibitor is an ATPase inhibitor and/or ADPase inhibitor, an UTPase inhibitor and/or UDPase inhibitor, a CTPase inhibitor and/or CDPase inhibitor, a TTPase inhibitor and/or TDPase inhibitor, or a GTPase inhibitor and/or GDPase inhibitor.

In another aspect of the method, the NTPDase inhibitor is an inhibitor of CD39, CD39L1, CD39L2, CD39L3, CD39L4, Golgi-associated ecto-ATPase and ecto-uridine diphosphatase (UDPase), lysosomal ecto-apryase LALP70, hepatic canalicular ecto-apyrase, α-sarcoglycan or potato apyrase.

In yet another aspect of the method, the NTPDase inhibitor is an antisense oligonucleotide. The antisense oligonucleotide comprises a nucleic acid that is complementary to the nucleic acid sequence encoding an ATPase and/or ADPase, an UTPase and/or UDPase, a CTPase and/or CDPase, a TTPase and/or TDPase, or a GTPase and/or GDPase or a fragment thereof.

In some embodiments of this method, the expression construct is a viral expression construct and may be a retroviral construct, an adenoviral construct, an adeno-associated viral construct, a herpesviral construct, a polyoma viral construct, and a vaccinia viral construct.

In other embodiments of the method, the expression construct is a non-viral expression construct. The non-viral expression construct may be administered either as a naked DNA construct or in a liposomal formulation.

The invention also provides methods of screening for modulators of NTPDase-mediated immune responses comprising: a) providing a cell that expresses a membrane bound NTPDase or an ecto-NTPDase; b) contacting the cell with a candidate substance; and c) determining the effect of the candidate substance on the NTPDase level in the cell, wherein a change in the level of a NTPDase in the cell, as compared to NTPDase level in the absence of the candidate substance, indicates that the candidate substance is a modulator of NTPDase level, and therefore a modulator of NTPDase-mediated immune responses.

In one embodiment of the invention, the cell is a dendritic cell. The dendritic cell can be a Langerhans cell or cell line. Examples of dendritic cell lines include the XS52 or the XS106 cell lines.

In another embodiment, the NTPDase is an ATPase and/or ADPase, an UTPase and/or UDPase, a CTPase and/or CDPase, a TTPase and/or TDPase, or a GTPase and/or GDPase.

In yet another embodiment of the method, the cell expresses an ATPase, an ADPase, an UTPase or an UDPase.

In another aspect of the invention, the cell comprises an expression construct comprising a DNA segment encoding the NTPDase under the control of a promoter active in the cell.

In one embodiment of the method, the determining comprises measuring NTPDase activity of the cell. The NTPDase activity can be measured by: a) culturing the cell in a culture solution comprising a nucleotide; b) determining the effect of the candidate substance on nucleotide levels in the culture solution; and c) measuring a change in the nucleotide levels in the culture solution as compared to nucleotide levels in the absence of the candidate substance.

The nucleotide is ATP and/or ADP and/or AMP, UTP and/or UDP and/or UMP, CTP and/or CDP and/or CMP, TTP and/or TDP and/or TMP, or GTP and/or GDP and/or GMP.

In some aspects, the AMP levels may be detected by chromatographic methods.

In other embodiments of the invention, the measuring comprises measuring the NTPDase levels on the surface of the cell. Such methods may comprise an enzyme linked immunoassay using an enzyme-labeled anti-NTPDase antibody. Some examples of anti-NTPDase antibodies that may be used include an anti-ATPase and/or anti-ADPase antibody, an anti-UTPase and/or anti-UDPase antibody, a anti-CTPase and/or anti-CDPase antibody, a anti-TTPase and/or anti-TDPase antibody, or a anti-GTPase and/or anti-GDPase antibody.

In another embodiment of the method, the measuring comprises fluorescent activated cell sorting of cells using a fluorescent-labeled anti-NTPDase antibody.

In one embodiment of the method, the determining comprises measuring the NTPDase mRNA level in the cell. In another embodiment of the method, the measuring comprises Northern blotting. In yet another embodiment of the method, the measuring comprises quantitative RT-PCR.

The invention also provides methods of screening for modulators of NTPDase-mediated immune responses comprising: a) providing a cell that comprises an expression construct comprising a DNA segment encoding a screenable marker under the control of a promoter for a NTPDase; b) contacting the cell with a candidate substance; and c) determining the effect of the candidate substance on expression of the selectable marker, wherein a change in the expression of the selectable marker, as compared to selectable marker expression in the absence of the candidate substance, indicates that the candidate substance is a modulator of NTPDase promoter expression, and therefore a modulator of NTPDase-mediated immune responses.

In one embodiment of this method, the NTPDase-mediated immune responses is an immune response mediated by an NTPDase such as CD39, CD39L1, CD39L2, CD39L3, CD39L4, Golgi-associated ecto-ATPase and ecto-uridine diphosphatase (UDPase), lysosomal ecto-apryase LALP70, hepatic canalicular ecto-apyrase, α-sarcoglycan or potato apyrase.

In another embodiment of this method, the screenable marker is an enzyme and the determining comprises measuring enzyme activity.

The invention also provides a method for treating a hyperactive immune response in a subject comprising administering to the subject a composition comprising a P2-receptor inhibitor.

In one embodiment of the invention, the P2-receptor inhibitor is an P2-receptor antagonist, an anti-P2-receptor antibody, an antisense P2-receptor oligonucleotide, or a chemical substance that inhibits a P2 receptor.

The P2-receptor inhibitor may be an inhibitor of any P2 receptor such as, but not limited to, $P2X_1$, $P2X_4$, $P2X_5$, $P2X_7$, $P2X_1$, $P2Y_1$, $P2Y_1$, $P2Y_2$, $P2Y_4$, $P2Y_5$, $P2Y_6$, $P2Y_{10}$, or $P2Y_{11}$.

In one embodiment of the method, the P2-receptor inhibitor is an P2-receptor antagonist and is exemplified in non-limiting examples by suramin, KN-62, MRS2179, TNP-ATP, TNP-GTP, oxidized ATP, PPADS, Reactive Blue2.

In another embodiment, the P2-receptor inhibitor is an antisense oligonucleotide composition and comprises a nucleic acid that is complementary to a nucleic acid sequence encoding a $P2X_1$, $P2X_4$, $P2X_5$, $P2X_7$, $P2X_1$, $P2Y_1$, $P2Y_1$, $P2Y_2$, $P2Y_4$, $P2Y_5$, $P2Y_6$, $P2Y_{10}$, or $P2Y_{11}$ receptor, or to a fragment thereof.

In one embodiment of the method, the hyperactive immune response is an allergic reaction and is exemplified by allergic contact dermatitis, atopic dermatitis, allergic rhinitis (hay fever), bronchial asthma and the like.

In another embodiment of the method, the hyperactive immune response is an autoimmune disease and is exemplified by Addison's disease, alopecia, ankylosing spondylitis, antiphospholipid syndrome, Behcet's disease, chronic fatigue syndrome, Crohn's disease, ulcerative colitis, diabetes, fibromyalgia, Goodpasture syndrome, Graves' disease, idiopathic thrombocytopenic purpura, lupus, Meniere's multiple sclerosis, myasthenia gravis, pemphigus vulgaris, primary biliary cirrhosis, psoriasis, rheumatoid arthritis, rheumatic fever, sarcoidosis, scleroderma, vasculitis, vitiligo, or Wegener's granulomatosis, etc.

It is contemplated that the P2-receptor inhibitor can be administered by topical, oral, intranasal, intratracheal, intraesophageal, intrabronchial, intra-vaginal, rectal intravenous, intraarterial, subcutaneous, or intramuscular routes.

The invention also provides a method for preventing a hyperactive immune response in a subject comprising administering to the subject a composition comprising a P2-receptor inhibitor.

Also provided is a method for treating or preventing a hyperactive immune response in a subject comprising administering to the subject an expression construct comprising a DNA segment encoding a P2-receptor inhibitor under the control of a promoter active in cells of the subject.

In one such embodiment, the P2-receptor inhibitor is an inhibitor of the $P2X_1$, $P2X_4$, $P2X_5$, $P2X_7$, $P2X_1$, $P2Y_1$, $P2Y_1$, $P2Y_2$, $P2Y_4$, $P2Y_5$, $P2Y_6$, $P2Y_{10}$, or $P2Y_{11}$ receptor. In another such embodiment, the P2-receptor inhibitor is an antisense oligonucleotide. The antisense oligonucleotide comprises a nucleic acid that is complementary to a nucleic acid sequence encoding a $P2X_1$, $P2X_4$, $P2X_5$, $P2X_7$, $P2X_1$, $P2Y_1$, $P2Y_1$, $P2Y_2$, $P2Y_4$, $P2Y_5$, $P2Y_6$, $P2Y_{10}$, or $P2Y_{11}$ receptor, or a fragment thereof.

In some aspects, the expression construct is a viral expression construct and may be selected from the group consisting of a retrovirus, an adenovirus, an adeno-associated virus, a herpesvirus, a polyoma virus, and a vaccinia virus.

In other aspects, the expression construct is a non-viral expression construct. The non-viral expression construct may be administered as a naked DNA or in a liposomal formulation.

The exact doses and routes of administration will be decided at the time of therapy by a trained physician depending on factors such as site of lesion or disease, health of the patient and other related factors.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A), Epidermal sheets prepared from the ear samples of $CD39^{+/+}$, $CD39^{+/-}$, or $CD39^{-/-}$ mice were stained for the indicated markers. The data shown are representative fields from three independent experiments (original magnification: ×200). (FIG. 1B), Surface densities of IA-, DEC205-, or Vγ3-positive epidermal cells were counted under a fluorescence microscope using an image analysis program. Data shown are the mean±SD (n=3) in a representative experiment. (FIG. 1C), Epidermal sheets prepared from the ear samples of $CD39^{+/+}$, $CD39^{+/-}$, or $CD39^{-/-}$ mice that were subjected to histo-enzymatic staining for ecto-NTPDase activities with the ATP or ADP substrate. The data shown are representative fields from three independent experiments after "overexposure" to detect any residual enzymatic activities.

(FIG. 2A), The indicated cell lines were subjected to histo-enzymatic staining for ecto-NTPDase activities with the ATP or ADP substrate. (FIG. 2B), The indicated cell lines were examined for CD39 mRNA expression by RT-PCR (30 cycles) (Enjyoji et al., 1999). (FIG. 2C), Membrane fractions isolated from the indicated cell lines were examined for CD39 protein expression by Western blot using polyclonal anti-CD39 antibodies (Enjyoji et al., 1999). (FIG. 2D), RNA isolated from the whole skin of $CD39^{+/+}$ mice (lane 1) or $CD39^{-/-}$ mice (lane 2) were examined for CD39 mRNA expression by RT-PCR. In parallel, epidermal cells isolated from $CD39^{+/+}$ mice were examined for CD39 mRNA expression before (lane 3) or after LC depletion with magnet beads coated with anti-IA antibody (lane 4). All data shown in this figure are representative of at least three independent experiments.

(FIG. 3A), Pam 212 keratinocytes were treated with croton oil (CO), benzalkonium chloride (BAC), or ethyl phenylpropiolate (EPP) at the indicated concentrations or exposed to UVB irradiation at the indicated doses. Culture supernatants were examined for ATP concentrations by the luciferin-luciferase assay and for LDH using the CytoTox 96 assay kit (Promega). (FIG. 3B), Pam 212 keratinocytes were incubated for 10 min with the indicated chemicals and examined for release of ATP and ADP into culture media. ADP concentrations were measured after pyruvate kinase-mediated conversion to ATP. (FIG. 3C), Pam 212 keratinocytes and XS52 LC were co-cultured at the indicated cell densities and treated for 10 min with PBS alone or with 0.0015% BAC. All data shown in this figure are representative sets of results (mean±SD, n=3) from three independent experiments. * p<0.05; ** p<0.01 (two-tailed Student's t-test).

FIG. 4D, Ear skin samples were harvested from $CD39^{+/+}$ or $CD39^{-/-}$ mice 5 days after topical application of vehicle alone or 1% CO and processed to histological analyses after H&E staining (original magnification: ×250). FIG. 4E, $CD39^{-/-}$ mice (n=6) or C57BL/6 wild-type mice (n=10) (FIG. 4F) received local injections of apyrase on the right ear (closed circles) or PBS alone on the left ear (open circles) before and after topical application of 1% CO on both ears. The data shown are the mean±SEM of the swelling responses (the ear thickness after CO application minus the baseline thickness before application) at the indicated time points. Statistical significant differences (one-tailed Student's t-test) are indicated by asterisks (*p<0.05 and **p<0.01). FIG. 4G, $CD39^{-/-}$ mice (circles), $CD39^{+/-}$ mice (triangles) or $CD39^{+/+}$ mice (squares) received a single dorsal irradiation of 1,500 $J/m^2$ of UVB radiation and examined for inflammatory responses. The data shown are the mean±SEM (n=10) of the swelling responses (the thickness after irradiation minus the baseline thickness before irradiation). FIG. 4H, $CD39^{-/-}$ mice (circles), $CD39^{+/-}$ mice (triangles) or $CD39^{+/+}$ mice (squares) were examined for allergic contact hypersensitivity responses to oxazolone (OX). The data shown are the mean±SEM (n=10) of the swelling responses (the thickness of OX-challenged right ear minus the thickness of vehicle-challenged left ear). All data shown in this figure are representative of at least two independent experiments.

(FIG. 5C) Mice received local injection of TNFα and examined for surface densities of IA+ epidermal cells (means±s.d., n=3). At 24 hr after topical application of FITC, the DLN were examined for the numbers of migratory LC (means±s.d., n=3) (FIG. 5D) localization of FITC+ migratory LC after counterstaining of the B cell areas with PE-conjugated B220 mAb (FIG. 5E), and for the surface phenotype of FITC+ migratory LC (FIG. 5F). Closed and open histograms represent the staining profiles with the indicated mAb and control IgG, respectively. Numbers in the parentheses indicate the mean fluorescence intensities (MFI). (FIG. 5G), Migratory LC isolated from OX-painted $CD39^{-/-}$ mice (circles) or $CD39^{+/+}$ mice (squares) were co-cultured with OX-reactive, wild-type T-cells. The data shown are the means±s.d. (n=3) of interferon-γ (IFN-γ) concentrations in the culture supernatants (* P<0.05). (FIG. 5H), Bone marrow-derived DC generated from $CD39^{-/-}$ mice (circles) or $CD39^{+/+}$ mice (squares) were pulsed with TNBS and injected into $CD39^{+/+}$ mice. The recipient animals were challenged with TNCB and examined for swelling responses (means±s.e.m., n=10) (* P<0.05 and ** P<0.01 between $CD39^{-/-}$ DC and $CD39^{+/+}$ DC).

(FIG. 6A), T-cells isolated from $CD39^{+/+}$ mice were stimulated with the indicated mAb in immobilized forms and examined for pericellular ATP concentrations (means±s.d., n=5) (* P<0.05 and  P<0.01). (FIG. 6B), Bone marrow-derived DC generated from $CD39^{-/-}$ mice (circles) or $CD39^{+/+}$ mice (squares) were incubated for 60 min in the presence of the indicated concentrations of ATP and then examined for cell viability (means±s.d., n=3) ( P<0.01 compared to the baseline cell viability). (FIG. 6C), $CD39^{-/-}$ or $CD39^{+/+}$ DC were pre-treated with apyrase or buffer alone and then examined for ATP-mediated activation responses. Data shown are the means±s.d. (n=3) of cell viability (left), IL-6 production (middle), and LY uptake (right). Statistically, significant differences are indicated by asterisks (** P<0.01). All data shown in this figure are representative of at least two independent experiments.

DETAILED DESCRIPTION OF THE INVENTION

Figure 1:
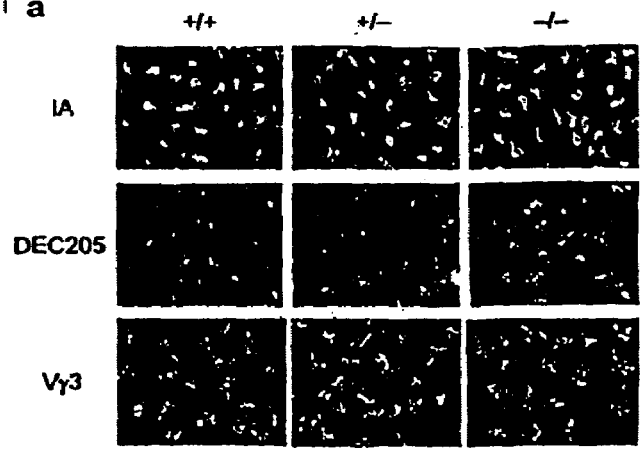
FIGS. 1A, 1B, & 1C. Lack of LC-associated ecto-NTPDase activities in CD39-deficient mice.
Figure 1:
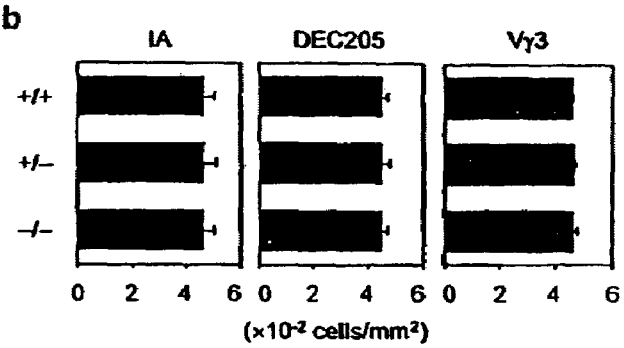
Figure 1:
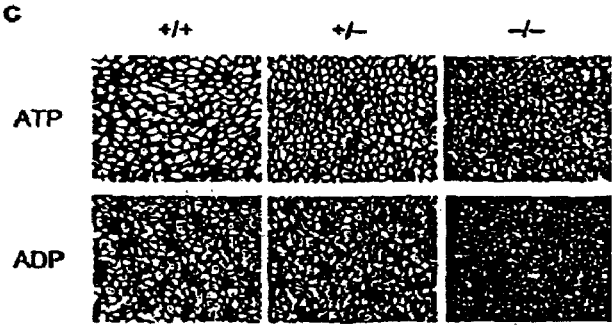

Langerhans cells (LC) are skin-specific members of the dendritic cell family of antigen presenting cells. Wolff & Winkelmann discovered, over thirty years ago, that LC defined under electron microscopy by the inclusion of Birbeck granules could be identified at the light microscopy level by ATPase staining (Wolff & Winkelmann, 1967). In this histo-enzymatic method, the ATP substrate is hydrolyzed in the presence of lead to form lead phosphate, and then converted to lead sulfide with ammonium sulfide. Deposition of lead sulfide granules observed along the plasma membrane at the exterior surface, indicates that LC express ecto-ATPase activity. Subsequently, LC were found to hydrolyze not only ATP, but also the ADP substrate in a divalent cation-dependent manner (Chaker et al., 1984).

Extracellularly released nucleotides, for example, ATP and ADP, are known to regulate many different forms of intercellular communication via binding to the ligand gated ion channel P2X receptors and G-protein coupled P2Y receptors (Williams and Jarvis, 2000). For example, ATP acts as a fast excitatory neurotransmitter in nervous tissue, with P2X and P2Y receptors being widely distributed on neurons, astroglia, microglia, and oligodendroglia. ATP and ADP are released from endothelial cells by mechanical shear forces, stretch, changes in osmolarity, oxidative stress, and microbial products (e.g., LPS), thereby exerting apoptotic, inflammatory, and thrombotic effects in the vascular system.

With respect to purinergic signaling in skin, in vitro treatment of keratinocytes with ATP has been reported to mobilize intracellular $Ca^{2+}$, inhibit terminal differentiation, affect proliferation, and induce apoptosis (Pillai and Bikle, 1992; Pillai, 1995; Sutter et al., 1991; Girolomoni, 1993). In 1999, five groups reported independently that dendritic cells (DC) express mRNA for a variety of P2 receptors ($P2X_1$, $P2X_4$, $P2X_5$, $P2X_7$, $P2X_1$, $P2Y_1$, $P2Y_1$, $P2Y_2$, $P2Y_4$, $P2Y_5$, $P2Y_6$, $P2Y_{10}$, and $P2Y_{11}$) and that ATP triggers $Ca^{2+}$ influx, phenotypic maturation, chemotactic migration, and apoptosis of DC, whereas ADP (as well as UTP and UDP) induces production of IL-1β, IL-6, IL-10, and IL-12 (p40) by DC (Mutini et al., 1999; Liu et al., 1999; Coutinho-Silva et al., 1999; Berchtold et al., 1999; Marriott et al., 1999).

The present inventors have determined that CD39, a vascular ecto-NTPDase, is responsible for the ADPase and ATPase functions of LC. This was accomplished by creating CD39 knockout mice that lacked one or both functional alleles for CD39. A comparison of the relative inflammatory responses of these animals to croton oil demonstrated that the double-knock out animals (i.e., the $CD39^{-/-}$ mice), had much stronger inflammatory responses than did normal animals, with the heterozygote (i.e., the $CD39^{+/-}$ mice), showing intermediate inflammation. Interestingly, all the animals were comparable in their response to UVB radiation-induced inflammation, which involves a non-ADP/ATP inflammatory pathway. Together, these data not only identify CD39 as responsible for the ADPase/ATPase function of LC, but indicate that nucleotides such as ADP/ATP (or UTP and UDP) act as specific mediators of chemically induced inflammation, and that CD39 is responsible for protection of animals from this response. Moreover, hydrolysis of extracellular ADP and ATP by LC-associated CD39 represents an important regulatory mechanism controlling the magnitude of inflammation in the skin.

The present inventors also examined allergic contact hypersensitivity responses, wherein hapten-pulsed LC play a pathogenic role by activating hapten-reactive T-cells. $CD39^{-/-}$, $CD39^{+/-}$, and $CD39^{+/+}$ mice were sensitized by topical application of oxazolone (OX), challenged 5 days later with the same hapten on ear skin, and ear swelling responses were measured. In marked contrast to the heightened inflammatory responses to irritant chemicals, immune responses to OX were severely attenuated in $CD39^{-/-}$ mice and the $CD39^{+/-}$ mice showed intermediate responses. These results demonstrate that LC-associated CD39 plays a unique role in cellular immune responses and reduces hyperactive immune responses.

Thus, the present inventors have also demonstrated that immune responses to reactive haptens are severely attenuated in $CD39^{-/-}$ mice and that T-cells increase pericellular ATP concentrations in response to CD3/TCR-mediated co-stimulatory signals. Furthermore, $CD39^{-/-}$ DC were found to be functionally impaired in their antigen presenting capacity. Based on these findings, the inventors contemplate that T-cell-derived ATP acts as a signaling molecule during antigen presentation and that this signaling pathway is regulated by CD39-mediated hydrolysis of excess amounts of ATP. This is further supported by the recent reports documenting that DC express mRNA for a variety of P2 receptors (e.g., $P2X_1$, $P2X_4$, $P2X_5$, $P2X_7$, $P2Y_1$, $P2Y_2$, $P2Y_4$, $P2Y_5$, $P2Y_6$, $P2Y_{10}$, and $P2Y_{11}$), and that DC respond to nucleotide stimulation by pore formation, $Ca^{2+}$ influx, phenotypic maturation, chemotactic migration, apoptosis, and cytokine production (Mutini et al., 1999; Liu et al., 1999; Coutinho-Silva et al., 1999; Berchtold et al., 1999; Marriott et al., 1999; Nihei et al., 2000; Ferrari et al., 2000).

Although, the mechanisms underlying the impaired antigen presenting capacity of CD39$^{-/-}$ DC remain to be fully elucidated, the inventors determined that CD39$^{-/-}$ DC are unresponsive to ATP-induced death and IL-6 production, while exhibiting intact pore formation after ATP stimulation. This indicates that one or more P2Y receptors, but not pore forming P2X receptors, are desensitized in CD39$^{-/-}$ DC. This is supported by reports that have documented a unique, P2Y$_1$ receptor-mediated apoptosis pathway and the involvement of a P2Y$_6$ receptor in nucleotide-induced IL-8 production (Sellers et al., 2001; Warny et al., 2001). The inventors are currently investigating the identity of the P2 receptor(s) that are desensitized in CD39$^{-/-}$ DC and the identity of the P2 receptors that are functionally involved in extracellular nucleotide-mediated DC:T-cell communication.

Thus, CD39 plays important roles in cellular immunity responses of DC and is required for proper antigen presentation and primary stimulation of hapten-reactive T-cells. Thus, the inventors contemplate that CD39 and other NTPDase inhibitors will be useful in preventing and/or treating hyperactive immune conditions such as allergic reactions, autoimmune conditions.

As P2-receptors are involved in nucleotide mediated signaling in dendritic cells, another embodiment of this invention provides P2-receptor inhibitors as therapeutics for NTPDase-mediated hyperactive immune responses.

Thus, the present invention describes the diverse roles of CD39 in regulating extracellular nucleotide-mediated signaling in inflammatory responses to environmental insults and in intercellular communication between DC and T-cells in the immune system.

I. NTPDases

NTPDases are a group of extracellular nucleotidase enzymes that are often membrane-bound. These enzymes have their active nucleotide hydrolysis sites facing the exterior of the cell. The NTPDases possess other unique characteristics besides an extracellular active site. They have a broad nucleotide substrate range (e.g. ATP and ADP, or UTP and UDP, etc. depending on the specific types of nucleotides hydrolyzed and therefore such enzymes are also called ATPase and/or ADPases; or UTPase and/or UDPase; GTPase and/or GDPases; CTPase and/or CDPases; TTPase and/or TDPases), a requirement for calcium or magnesium for activity, and insensitivity to many of the classic inhibitors effective against the mitochondrial, lysosomal, and plasma membrane ATPases. They are also present in cells in extremely low amounts, making the isolation and definitive identification of them very difficult until recently.

Some non-limiting examples of the NTPDases include CD39, CD39L1, CD39L2, CD39L3, CD39L4, Golgi-associated ecto-ATPase and ecto-uridine diphosphatase (UDPase), lysosomal ecto-apyrase LALP70, hepatic canalicular ecto-apyrase, α-sarcoglycan and potato apyrase.

The NTPDases are involved in a large number of physiological functions. Several NTPDases are found in vascular endothelial cells, smooth muscle cells, and in the heart (Yeung et al., 2000). It is believed that these enzymes inactivate extracellular nucleotide signals in both, the cardiovascular system and associated smooth muscle. Extracellular nucleotides like ATP are effective regulators of blood vessel vascular tone by their ability to bind to specific purine receptors, causing blood vessels to dilate in some instances and to constrict in other cases. This directly modulates blood pressure. The NTPDase ectonucleotidases are involved in the control of vascular tone by regulating the level of circulating ATP.

NTPDase 1, also called, CD39, has been shown to play an important role in maintaining blood hemostasis and preventing thrombosis. NTPDase activity hydrolyzes ADP, which is an important coagulant of blood platelets, thereby modulating blood clotting. Soluble forms of NTPDases have been found in the salivary glands of blood-feeding insects such as mosquitoes, ticks, bedbugs etc.

NTPDases are also found in the brain. Extracellular nucleotides interact with and activate nucleotide type 2 (P2) receptors in the brain that initiate a wide variety of signaling pathways, important for functional associations between neurons and glial cells and for the regulation of blood flow, haemostatic and inflammatory reactions in the brain.

Ecto-NTPDase activities have also been widely used as markers of epidermal Langerhans cells, which are skin-specific members of the dendritic cell family of antigen presenting cells.

Some known NTPDase antagonists include Azide, Evans Blue, Suramin, PPADS, DEPC, P-CMPS, P-HMB, NP-40, FSBA (Knowles et al., 1999; Heine et al., 1999; Zinchuk et al., 1999; Dumbrowski et al., 1998).

(i) ADPases and ATPase

ADPases and ATPases are NTPDase enzymes that convert the substrates adenosine di-phosphate (ADP) or adenosine tri-phosphate (ATP) to adenosine mono-phosphate (AMP) by a hydrolysis reaction. Of particular interest in the present invention is the ecto-ATPase CD39. CD39 also has UTPase and/or UDPase activity and the present inventors envision the use of this activity in relation to this invention as well.

CD39 was originally identified as an obscure activation marker expressed on B cells, T-cells, natural killer cells, dendritic cells and endothelial cells (Maliszewski et al., 1994; Kansas et al., 1991). More recently, it has been found to be responsible for the ecto-NTPDase activity on endothelial cells (Kaczmarek et al., 1996; Wang & Guidotti, 1996).

Other CD39-like transcripts have been characterized since and include, CD39L1, CD39L2, CD39L3, and CD39L4, all of which share extensive amino acid homology with other nucleotide triphosphatases in vertebrates, invertebrates, as well as plants, indicating that these genes also encode proteins with ecto-nucleotidase activity (Chadwick et al., 1998). The expression pattern of five human members of this gene family maps these genes to a region associated with audiogenic seizure susceptibility in mouse. CD39 family members have also been shown to be expressed in microglia and in the cerebrovascular endothelial and smooth muscle cells (Braun et al., 2000), where they are believed to regulate P2 receptor-mediated functions of microglia and blood flow and thrombogenesis. CD39L2 proteins are found in the heart muscle and capillary endothelial cells (Yeung et al., 2000).

In relation to the present invention, any NTPDase may be involved or used in the either the assay; and/or the screening methods; and/or the therapies described above, including CD39, CD39L1, CD39L2, CD39L3, CD39L4, Golgi-associated ecto-ATPase and ecto-uridine diphosphatase (UDPase), lysosomal ecto-apyrase LALP70, hepatic canalicular ecto-apyrase, α-sarcoglycan and potato apyrase as some non-limiting examples.

II. P2 Receptors

Membrane-bound P2-receptors mediate the actions of extracellular nucleotides in cell-to-cell signaling. Two main families of P2 receptors are known, the P2X-receptors which are ligand-gated ion channels, and the P2Y-receptors which are G-protein-coupled receptors. To date, eight subtypes of the P2Y family have been cloned and functionally characterized.

DC are known to express mRNA for a variety of P2 receptors including the $P2X_1$, $P2X_4$, $P2X_5$, $P2X_7$, $P2Y_1$, $P2Y_2$, $P2Y_4$, $P2Y_5$, $P2Y_6$, $P2Y_{10}$, and the $P2Y_{11}$ receptors. Furthermore, DC respond to nucleotide stimulation by pore formation, $Ca^{2+}$ influx, phenotypic maturation, chemotactic migration, apoptosis, and cytokine production which are the characteristic responses of P2 receptors (Mutini et al., 1999; Liu et al., 1999; Coutinho-Silva et al., 1999; Berchtold et al., 1999; Marriott et al., 1999; Nihei et al., 2000; Ferrari et al., 2000).

The present inventors have shown that P2 receptors are involved in DC and T-cell communication and have found that the P2Y receptors are desensitized in CD39 knockout mice.

Some of the known P2 receptor antagonists include suramin, KN-62, MRS2179, TNP-ATP, TNP-GTP, oxidized ATP, PPADS, Reactive Blue2 (Williams et al., 2000; Ralevic et al., 1998).

III. Screening for Nucleotide Release

Irritant contact dermatitis is the most frequently observed occupational health problem among factory workers. No in vitro tests are currently available to predict relative skin irritant potentials of industrial and environmental chemicals. Many attempts to create such assays by companies have, in fact, failed. This may be due, at least in part, to the lack of information on the patho-physiology of irritant contact dermatitis.

In some embodiments, the present inventors have developed an assay to measure the irritant potential of various chemicals. The assay relies on measurement of nucleotide release by cells. Any cell that can release a nucleotide, such as, ATP and/or ADP and/or AMP; UTP and/or UDP and/or UMP; CTP and/or CDP and/or CMP; GTP and/or GDP and/or GMP; TTP and/or TDP and/or TMP, in response to a chemical irritant can be used for such an assay and are exemplified in non-limiting examples by keratinocytes, fibroblast cells, PAM 212 cells, dendritic cells, and cell lines thereof. As such, the assay is only applicable to those irritants that act through the nucleotide pathway.

In other embodiments, this assay is used to measure the NTPDase activity of a cell in response to various candidate substances that may be potential modulators of NTPDase-mediated immune responses. Such modulators of NTPDase expression or activity or function are contemplated to be useful in the prevention and/or treatment of hyperactive immune conditions such as autoimmune diseases and allergies.

One example of an assay used to measure the release of ATP by cells is based on the enzymatic luciferin-luciferase assay (Lust et al. 1981; Lundin 1993). The luciferin-luciferase assay is based on the ability of the firefly enzyme, luciferase, to catalyze the luminescent reaction of luciferin with ATP and oxygen to product light which is described by the reaction:

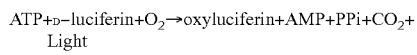
ATP+D-luciferin+$O_2$→oxyluciferin+AMP+PPi+$CO_2$+ Light

As the amount of ATP is directly proportional to the light emitted, quantification of the emitted light provides a measure of the amount of ATP. This assay has been suitably modified for measuring ATP release by cells. Initially, a standard curve is plotted, using ATP standard solutions (made of several known concentrations of ATP), and a fixed amount of luciferin (enzyme) and luciferase (substrate). A luminometer is typically used to quantitate the amount of light released by different concentrations of ATP when incubated with luciferin and luciferase. Cellular ATP release is then measured by: obtaining cells growing in culture; replacing the culture medium with a buffer; adding the ATP releasing agent (chemical irritant or a modulator of an NTPDase-mediated immune response); obtaining a sample of the buffer surrounding the cells after allowing sufficient time for ATP release by the cell in response to the irritant or modulator of an NTPDase-mediated immune response; adding luciferin and luciferase to this buffer; and quantitating the light released using a luminometer. A negative control can comprise obtaining the same reading with no cells; and/or obtaining the same reading with no added ATP releasing agent. The data are then analyzed by comparing to the standard ATP curve. Generally the cells in such assays may be grown in a multi-well format.

Other methods used to quantify and/or measure the release of ATP and/or ADP by cells include a wide variety of chromatographic procedures. Such chromatographic methods are well known in the art. For example, liquid chromatographic procedures are commonly used to separate and measure levels of ADP and/ATP. High-performance liquid chromatography, in one specific example, can use a partisil 10 SAX Whatman column (Whatman Inc, Clifton, N.J.) in 0.25 mol/L potassium phosphate monobasic (pH 6.5) at a flow rate of 1.5 mL/min to separate and quantify ATP and/or ADP levels. Chromatograms can be analyzed using computerized software and by comparison with standard curves made by performing serial dilutions for known concentrations of ATP and/or ADP. In another example, boronate chromatography using a boronate-derivatized cation-exchange resin (for example, Bio-Rex 70) can be used to separate ADP and/or ATP. Elution buffers vary greatly depending on the type of chromatography. In the case of boronate-derivatized cation-exchange the elution buffers can comprise ethanol and ammonium acetate. Picomole amounts of products are detectable making the assays sensitive. Yet other examples use thin-layer chromatography (TLC) methods.

Additionally, the release of ADP into culture media can be measured by the pyruvate kinase-mediated conversion to ATP. This enzymatic assay utilizes pyruvate kinase (PK) which catalyzes the following reaction:

Phospho(enol)pyruvate+ADP→Pyruvate+ATP

Pyruvate kinase is a key enzyme in glucose metabolism pathway. Mammalian PK enzymes isolated from different tissues have distinct characteristics which are related to the specific metabolic requirements of each tissue. Generally, PK isolated or prepared from rabbit muscle, is extensively used in the quantitative determination of ADP and of enzymes that catalyze the formation of ADP. It is contemplated that any form of PK, from any source can be used to determine the concentration of ADP in context of the present invention.

IV. Vectors for Delivery of NTPDases, NTPDase Inhibitors, or P2 Receptor Inhibitors Within certain embodiments, expression vectors are employed to express a NTPDase polypeptide product, for example, an ATPase or ADPase polypeptide. In other embodiments of the invention, expression vectors are used to express a NTPDase inhibitor or a P2 receptor inhibitor.

Such inhibitors are exemplified by antisense oligonucleotides complementary to a NTPDase or to a P2 receptor, expression vectors encoding an antibody against a NTPDase or a P2 receptor, expression vectors encoding a peptide, polypeptide, or protein encoding an inhibitor or antagonist of a NTPDase or a P2 receptor.

Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

(i) Regulatory Elements

Throughout this application, the term "expression construct" is meant to include any type of genetic construct containing a nucleic acid coding for a gene product in which part or all of the nucleic acid encoding sequence is capable of being transcribed and translated into a polypeptide product. An "expression cassette" is defined as a nucleic acid encoding a gene product under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In certain embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 2 and 3 list several regulatory elements that may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 1 and Table 2). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 1

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine | Jaynes et al., 1988; Horlick et al., 1989; Johnson |

TABLE 1-continued

Promoter and/or Enhancer

| Promoter/Enhancer | References |
|---|---|
| Kinase (MCK) | et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

Inducible Elements

| Element | Inducer | References |
|---|---|---|
| MT II | Phorbol Ester (TFA) | Palmiter et al., 1982; Haslinger et al., 1985; |
| | Heavy metals | Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| CRP | IL-6, IL-1 | Ku & Mortensen, 1993 |
| SAA | IL-6, IL-1 | Jiang et al., 1995 |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | TPA | Hensel et al., 1989 |
| Thyroid Stimulating Hormone α Gene | Thyroid Hormone | Chatterjee et al., 1989 |

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

(ii) Selectable Markers

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

(iii) Polyadenylation Signals

In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

(iv) Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (1989) and Ausubel et al. (1994), both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

(v) Delivery of Expression Vectors

There are a number of ways in which expression vectors may be introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

Adenovirus. One of the methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell innoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{12}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus & Horwitz, 1992; Graham and Prevec, 1991). Recently, animal studies suggested that recombinant adenovirus could be used for gene therapy (Stratford-Perricaudet & Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

Retrovirus. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Adeno-Associated Viruses. Adeno-associated virus (AAV) is an attractive virus for delivering foreign genes to mammalian subjects (Ridgeway, 1988; Baichwal and Sugden, 1986; Hermonat and Muzycska, 1984). AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription. The sequence of AAV is provided by U.S. Pat. No. 5,252,479 (entire text of which is specifically incorporated herein by reference).

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42–46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of the AAV vector of the present invention can be obtained by restriction endonuclease digestion of AAV or a plasmid such as p201, which contains a modified AAV genome (Samulski et al., 1987). Alternatively, the terminal repeats may be obtained by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

Other Viruses. Other viral vectors may be employed as expression constructs in the present invention. Vectors derived from viruses such as vaccinia virus (Ridgeway, 1988; Baichwal and Sugden, 1986; Coupar et al., 1988) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

Non-Viral Methods. Several non-viral methods for the transfer of expression constructs into mammalian cells also are contemplated by the present invention. These include DEAE-dextran (Gopal, 1985), electroporation (Tur-Kaspa et al., 1986; Potter et al., 1984), direct microinjection (Harland and Weintraub, 1985), lipofectamine-DNA complexes, cell sonication (Fechheimer et al., 1987), and receptor-mediated transfection (Wu and Wu, 1987; Wu and Wu, 1988).

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Liposomes. In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are Lipofectamine®-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ).

This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0 273 085).

In other embodiments, the delivery vehicle may comprise a ligand and a liposome. For example, Nicolau et al. (1987) employed lactosyl-ceramide, a galactose-terminal asialgan-glioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes. For example, epidermal growth factor (EGF) may be used as the receptor for mediated delivery of a nucleic acid into cells that exhibit upregulation of EGF receptor. Mannose can be used to target the mannose receptor on liver cells.

V. Methods for Preventing and Treating Chemically Induced Inflammation or a Hyperactive Immune Disorder (i) Protein Therapy One method for preventing and/or treating chemically induced inflammation is the provision, to a subject, of a polypeptide encoding a NTPDase such as an ATPase or an ADPase activity or an UTPase or UDPase activity and the like, that provides therapy for chemically induced inflammation. Such polypeptides may encode the entire enzyme or a fragment of the enzyme. For example, the fragment may encode a catalytically active fragment for the enzyme.

In other embodiments of the invention that are directed towards preventing and/or treating hyperactive immune disorders, such as, autoimmune diseases and/or allergies, a polypeptide encoding a NTPDase inhibitor or a P2 receptor inhibitor will be provided to a subject in need thereof. Such polypeptides may encode the entire inhibitory molecule or a fragment comprising the active domains of such an inhibitory molecule. Examples of such therapeutic peptides include peptides that are antagonists of a NTPDase or a P2 receptor, antibodies to an NTPDase or a P2 receptor, or any peptide or protein that interferes with the activity or levels of a NTPDase or a P2 receptor.

Alternatively, the therapeutic polypeptides described herein can be a synthetic peptide, a mimetics or any other analog thereof. The polypeptide may be produced by recombinant expression means or, if small enough, generated by an automated peptide synthesizer. Formulations would be selected based on the route of administration and purpose including but not limited to liposomal formulations and classic pharmaceutical preparations.

(ii) Gene Therapy

Another set of therapeutic embodiments contemplated by the present invention is the intervention, at the molecular level, in the events involved in chemically induced inflammation. Specifically, in some embodiments, the present inventors intend to provide, to an inflamed cell, an expression construct that provides a NTPDase activity, for example, an ATPase or ADPase activity, or function to that cell.

In other therapeutic embodiments, the invention contemplates, providing to a subject in need, an expression construct that expresses a NTPDase inhibitor or a P2 receptor inhibitor to treat or prevent a hyperactive immune response such as an allergic reaction or an autoimmune condition. These expression constructs will encode antisense oligo-nucleotides that are complementary to a NTPDase such as an ATPdase and/or ADPase, an UTPase and/or UDPase, a CTPase and/or CDPase, a TTPase and/or TDPase, or a GTPase and/or GDPase or a fragment thereof. The expression constructs may also encode for any peptide or protein that otherwise inhibits the function or activity or expression of a NTPDase. In still other embodiments, the expression construct will encode an antisense oligonucleotide complementary to a P2 receptor and/or will encode for a peptide or protein that inhibits the function or expression of a P2 receptor.

Because the sequence homology between the human, mouse, rat, rabbit, murine, primate and dog genes, any of the nucleic acids in these expression constructs could be used in human therapy, as could any of the gene sequence variants which would encode the same, or a biologically equivalent polypeptide. The lengthy discussion above of expression vectors and the genetic elements employed therein is incorporated into this section by reference. Particularly preferred expression vectors are viral vectors.

Those of skill in the art are well aware of how to apply gene delivery to in vivo and ex vivo situations. For viral vectors, one generally will prepare a viral vector stock. Depending on the kind of virus and the titer attainable, one will deliver 1 to 100, 10 to 50, 100–1000, or up to $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, or $1 \times 10^{12}$ infectious particles to the patient. Similar figures may be extrapolated for liposomal or other non-viral formulations by comparing relative uptake efficiencies. Formulation as a pharmaceutically acceptable composition is discussed below.

Various routes of delivery are contemplated. The vector may be delivered systemically or directly at the inflammation site by local and regional approaches. In some embodiments of the present invention, a subject is exposed to a viral vector and the subject is then monitored for expression construct-based toxicity, where such toxicity may include, among other things, causing a condition that is injurious to the subject.

(iii) Combination Therapies with Other Anti-Inflammatory Agents

The gene and/or protein based therapies of the present invention that are directed towards chemical inflammation can be used in conjunction with other therapies that are used for the treatment of inflammation. Thus, one may use a nucleic acid construct encoding a NTPDase activity and/or a polypeptide encoding the NTPDase activity in combination with an anti-inflammatory agent. Anti-inflammatory agents are agents that decrease the signs and symptoms of inflammation. A wide variety of anti-inflammatory agents are known to one of skill in the art. Most commonly used are the nonsteroidal anti-inflammatory agents (NSAIDs) which work by inhibiting the production of prostaglandins. Non-limiting examples include, ibuprofen, ketoprofen, piroxicam, naproxen, naproxen sodium, sulindac, aspirin, choline subsalicylate, diflunisal, oxaprozin, diclofenac sodium delayed release, diclofenac potassium immediate release, etodolac, ketorolac, fenoprofen, flurbiprofen, indomethacin, fenamates, meclofenamate, mefenamic acid, nabumetone, oxicam, piroxicam, salsalate, tolmetin, and magnesium salicylate. Another group of anti-inflammatory agents comprise steroid based potent anti-inflammatory agents, for example, the corticosteroids which are exemplified by dexamethason, hydrocortisone, methylprednisolone, prednisone, and triamcinolone as non-limiting examples. Several of these anti-inflammatory agents are available under well known brand names, for example, the NSAIDs comprising ibuprofen include Advil, Motrin IB, Nuprin; NSAIDs comprising acetaminophens include Tylenol; NSAIDs comprising naproxen include Aleve.

It is conceivable that more than one administration of either the other anti-inflammatory agent and the gene and/or protein-based therapy of the present invention will be required to achieve complete cure. Thus, various combinations may be employed, where the other anti-inflammatory agent is "A" and the NTPDase-based gene or protein therapy of the present invention is "B", as exemplified below:

A/B/A B/A/B B/B/A A/A/B B/A/A A/B/B B/B/B/A B/B/A/B

A/A/B/B A/B/A/B A/B/B/A B/B/A/A B/A/B/A B/A/A/B

B/B/B/A A/A/A/B B/A/A/A A/B/A/A A/A/B/A A/B/B/B

B/A/B/B B/B/A/B

Other combinations are also contemplated.

(iv) Kits for Administering NTPDases or Vectors Coding Therefor

The present invention also provides therapeutic kits. In some embodiment, such kits will generally contain, in suitable container means, a pharmaceutically acceptable formulation of a NTPDase, or a vector or vectors encoding a NTPDase in a form suitable for administration to a subject. In other embodiments, such kits will contain, in suitable container means, a pharmaceutically acceptable formulation of a NTPDase inhibitor, or a vector or vectors encoding a NTPDase inhibitor in a form suitable for administration to a subject. In still other embodiments, such kits will generally contain, in suitable container means, a pharmaceutically acceptable formulation of a P2 receptor inhibitor, or a vector or vectors encoding a P2 receptor inhibitor in a form suitable for administration to a subject. The kits may also contain other pharmaceutically acceptable formulations, such as buffers or agents that increase gene uptake or expression.

The kits may have a single container means that contains the enzyme or expression construct in a form suitable for administration. Other kits of the present invention include the enzyme (NTPDase) or inhibitor (NTPDase inhibitor or P2 receptor inhibitor) or expression construct expressing the enzyme or inhibitor in a storage stable form, along with buffers or diluents in separate and distinct containers. For example, when the components of the kit are provided in one or more liquid solutions, the liquid solution is an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container means.

The container means of the kit may also include at least one device for administration of the enzyme or inhibitor or expression construct encoding the enzyme or inhibitor. For example, a syringe or inhaler may be included. In some embodiments, the enzyme or expression construct may be pre-mixed and aliquoted into a unit dosage form and loaded into such a device. The kits may contain multiple devices for repeat administration or administration to more than one subject.

The kits of the present invention will also typically include a means for containing the vials, devices or such in close confinement for shipment, storage or commercial sale, such as, e.g., injection or blow-molded plastic containers into which the desired vials and other apparatus are placed and retained. The kits also may contain instructions for administration, including self-administration.

(v) Pharmaceutical Compositions

Where clinical applications are contemplated, it will be necessary to prepare pharmaceutical compositions comprising the therapeutic protein(s), and/or therapeutic nucleic acid(s), and/or therapeutic antibodies, and/or expression vectors, and/or virus stocks, and/or drugs, in a form appropriate for the intended application. Generally, this will entail preparing compositions that are essentially free of pyrogens, as well as other impurities that could be harmful to humans or animals.

One will generally desire to employ appropriate salts and buffers. Buffers also will be employed when recombinant cells are introduced into a patient. Aqueous compositions of the present invention comprise an effective amount of the proteins, vectors or drugs to a patient, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

Administration of these compositions according to the present invention will be via any common route so long as the target tissue is available via that route. This includes oral, nasal, buccal, rectal, vaginal or topical. Alternatively, administration may be by intradermal, subcutaneous, intramuscular, intraperitoneal or intravenous injection. Such compositions would normally be administered as pharmaceutically acceptable compositions, described supra. Of particular interest is direct topical administration to an affect area of the skin.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The composition may be formulated as a "unit dose." For example, one unit dose could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

VI. Screening for Modulators of Inflammatory and/or Hyperactive Immune Responses In another aspect of the invention, there is provided a method for screening for modulators of inflammatory responses that involve the induction of nucleotide release from keratinocytes. Nucleotides include any NTP and/or NDP and/or NMP, for example, ATP and/or ADP and/or AMP, UTP and/or UDP and/or UMP, CTP and/or CDP and/or CMP, TTP and/or TDP and/or TMP, GTP and/or GDP and/or GMP. The inventors envision that various different kinds of molecules may have an impact on nucleotide levels, and thereby affect the cellular inflammatory response that these molecules trigger. For example, one may envision providing a modulator that increases NTPDase activity. The increase in activity may be due to increased production of NTPDase, increased half-life of NTPDase, or combinations thereof, which cause higher levels of NTPDase enzyme to be present. Alternatively, other compounds may directly increase the activity of a NTPDase by acting to stabilize the enzyme structure or otherwise catalyze the hydrolysis of the nucleotide including the NDP and/or NTP to NMP, for example, ADP and/or ATP to AMP. Of course, decreases in all of these functions may be of interest as well.

In yet other aspects of the invention, there are provided methods for screening for modulators of NTPDase-mediated immune responses wherein the modulator changes the level or activity of a NTPDase. In some specific embodiments, the screening is performed in dendritic cells such as Langerhans and/or dendritic cell lines such as XS52 or XS106. Alternatively, the screening can be performed in any cell that expresses an NTPDase or even in any cell that is engineered to express an NTPDase. Changes in the NTPDase levels of a cell can affect its immune response, for example, increases in the cellular levels of NTPDase in certain cases leads to an hyperactive immune response. Thus, one may envision providing to a subject suffering from a hyperactive immune condition, such as an allergic reaction or an autoimmune condition a modulator that decreases NTPDase levels and activity. The decrease in activity may be due to a decrease in the production of NTPDase, inhibition of the NTPDase activity by inhibitors, suicide substrates, antagonists, or combinations thereof, or antibodies that bind to and inhibit the function of an NTPDase, all of which will ultimately decrease the levels and/or activity of the NTPDase enzyme.

(i) Assays for Changes in NTPDase Levels

Thus, in one embodiment, one may look directly at a candidate modulator's ability to affect the levels of a NTPDase. 'Candidate modulators' are defined herein as molecules that are either 'modulators of inflammation' or 'modulators of a NTPDase-mediated immune response' depending on the specific embodiment of the invention under consideration. One may look at mRNA levels to determine whether there are changes in transcription of a NTPDase. Alternatively, one may choose to look at protein levels of the NTPDase.

Assays for mRNAs. In some embodiments, one will examine levels of mRNA of an NTPDase. In such embodiments it will be advantageous to employ nucleic acid sequences, i.e., probes, in combination with an detection appropriate means, such as a label, for determining hybridization and quantification thereof. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means visible to the human eye or spectrophotometrically, to identify specific hybridization with complementary nucleic acid-containing samples.

Chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography. Electrophoresis also is a convenient method for separation.

In a particular embodiment, detection is by Northern blotting and hybridization with a labeled probe. The techniques involved in Northern blotting are well known to those of skill in the art and can be found in many standard books on molecular protocols. Sambrook et al., 1989. Briefly, mRNA products are separated by gel electrophoresis. The gel is then contacted with a membrane, such as nitrocellulose, permitting transfer of the nucleic acid and non-covalent binding. Subsequently, the membrane is incubated with a probe that is capable of hybridizing with a RNA product. Detection is by appropriate means, usually exposure of the membrane to x-ray film or ion-emitting detection devices. One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Quantitative RT-PCR. Reverse transcription (RT) of RNA to cDNA followed by relative quantitative PCR™ (RT-PCR™) can be used to determine the relative concentrations of specific mRNA species isolated from patients. By determining that the concentration of a specific mRNA species varies, it is shown that the gene encoding the specific mRNA species is differentially expressed.

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR™ products and the relative mRNA abundances is only true in the linear range of the PCR™ reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR™ for a collection of RNA populations is that the concentrations of the amplified PCR™ products must be sampled when the PCR™ reactions are in the linear portion of their curves.

The second condition that must be met for an RT-PCR™ experiment to successfully determine the relative abundances of a particular mRNA species is that relative concentrations of the amplifiable cDNAs must be normalized to some independent standard. The goal of an RT-PCR™ experiment is to determine the abundance of a particular mRNA species relative to the average abundance of all mRNA species in the sample. In the experiments described below, mRNAs for β-actin, asparagine synthetase and lipocortin II were used as external and internal standards to which the relative abundance of other mRNAs are compared.

Most protocols for competitive PCR™ utilize internal PCR™ standards that are approximately as abundant as the target. These strategies are effective if the products of the PCR™ amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR™ assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR™ is performed as a relative quantitative RT-PCR™ with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies may be performed using a more conventional relative quantitative RT-PCR™ assay with an external standard protocol. These assays sample the PCR™ products in the linear portion of their amplification curves. The number of PCR™ cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR™ assays can be superior to those derived from the relative quantitative RT-PCR™ assay with an internal standard.

One reason for this advantage is that without the internal standard/competitor, all of the reagents can be converted into a single PCR™ product in the linear range of the amplification curve, thus increasing the sensitivity of the assay. Another reason is that with only one PCR™ product, display of the product on an electrophoretic gel or another display method becomes less complex, has less background and is easier to interpret.

Immunoassays. The use of antibodies of the present invention in various immunologic assays are contemplated. In particular, ELISA assays will be utilized. Anti-NTPDase antibodies, such as anti-ATPase/ADPase, etc., will be immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for Cardi-Act or a fragment thereof that differs from the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° C. to about 27° C. Following incubation, the antisera-contacted surface is washed so as to remove non-immunocomplexed material. A preferred washing procedure includes washing with a solution such as PBS/Tween®, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The present inventors also contemplate use of immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard.

(ii) Measurements of NTPDase Activity

In some embodiments of the present invention, assays that measure the enzymatic activity of the NTPDase activity of a cell following contacting, or exposure, or treatment of the cell with a candidate chemical substance that has an irritant potential are contemplated. In other embodiments, screening methods to identify modulators of NTPDase-mediated immune responses involve assays that measure the enzymatic activity of a NTPDase in a cell following contacting, or exposure, or treatment of the cell with a candidate modulator of a NTPDase-mediated immune response.

NTPDase activity is the ability to hydrolyse a nucleotide triphosphate (NTP) into nucleotide diphosphate (NDP) and inorganic phosphate, or into nucleotide monophosphate (NMP) and pyrophosphate and/or the ability of the NTPDase to hydrolyse NDP into NMP and inorganic phosphate. Assays for NTPDase activity generally detect, measure or quantify the release of one or more of these reaction products. Hence, these assays measure changes in the amounts of NTP, and/or NDP, and/or NMP, and/or pyrophosphate, and/or inorganic phosphate as a result of enzyme activity and nucleotide cleavage.

(a) Assays for ADP/ATP Conversion to AMP

In some specific embodiments of the present invention, the NTPDase is an ATPase and/or a ADPase and assays that measure the enzymatic activity of the ATPase and/or ADPase activity of a cell following contacting, or exposure, or treatment of the cell with a candidate chemical substance that has an irritant potential are contemplated. In other embodiments, the chemical substance has the ability to modulate an NTPDase-mediated immune response. The ATPase activity is the ability to hydrolyse adenosine triphosphate (ATP) into adenosine diphosphate (ADP) and inorganic phosphate, or into adenosine monophosphate (AMP) and pyrophosphate. The ADPase activity is the ability to hydrolyse ADP into AMP and inorganic phosphate. These are described by the following reactions:

$$ATP + H_2O \rightarrow ADP + P_1$$

$$ADP + H_2O \rightarrow AMP + P_i$$

Assays for ATPase and/or ADPase activity generally detect, measure or quantify the release of one or more of these reaction products. Hence, these assays measure changes in the amounts of ATP, and/or ADP, and/or AMP, and/or pyrophosphate, and/or inorganic phosphate as a result of enzyme activity and ATP or ADP cleavage.

One such method is based on the enzymatic luciferin-luciferase assay described in detail above. This assay, used to measure the ATPase activity and also to measure ATP levels, is also described in Lust et al. (1981) and Lundin (1993), both incorporated herein by reference. This assays for ATP quantification is well known in the art. Another enzyme-based assay that can be used to measure nucleotide concentration is the pyruvate kinase assay. This well known assay has been used in the art to measure and quantify ADP levels.

Other methods involve the quantification or measuring of any hydrolysis product of ATP or ADP for example, ADP, AMP, inorganic phosphate and/or pyrophosphate. A wide variety of chromatographic procedures can be used for such purposes and are known to the skilled artisan. For example, liquid chromatographic procedures are commonly used to separate and measure levels of AMP, ADP and ATP. High-performance liquid chromatography, in one specific example, can use a partisil 10 SAX Whatman column (Whatman Inc, Clifton, N.J.) in 0.25 mol/L potassium phosphate monobasic (pH 6.5) at a flow rate of 1.5 mL/min to separate and quantify ATP and ADP levels. An EQC 5u S C18 column (Whatman Inc) in 0.25 mol/L ammonium phosphate monobasic (pH 4.5) at a flow rate of 2.0 mL/min can be used to measure AMP levels. Chromatograms can be analyzed using computerized software and by comparison with standard curves made by performing serial dilutions for known concentrations of ATP, ADP, and AMP. In another example, boronate chromatography using a boronate-derivatized cation-exchange resin (for example, Bio-Rex 70) can be used to separate one or more of the reaction products including, AMP, ADP, and ATP. Elution buffers vary greatly depending on the type of chromatography. In the case of boronate-derivatized cation-exchange the elution buffers can comprise ethanol and ammonium acetate. Picomole amounts of products are detectable making the assays sensitive. Still other examples use thin-layer chromatography (TLC) methods.

The amounts of $P_i$ can be measured by several methods known to the skilled artisan. For example, one may use the Taussky-Shorr reagent, or one may use the Malachite Green technique.

Yet other chromatographic methods to detect ATPase and ADPase activities are known in the art. One of ordinary skill in the art will recognize that any of these methods may be used to measure, detect and/or quantitate the ATPase and/or ADPase activities as required by the present invention, and one is not limited by the method of measuring.

In context of the present invention the measurements of nucleotides, i.e., ATP, ADP, AMP, pyrophosphate or inorganic phosphate released can be used to measure either the NTPDase activity in a cell or in response to NTPDase activity on the cell surface. In the latter case nucleotide, pyrophosphate or inorganic phosphate released into the extracellular medium is measured.

(b) Assays to Measure UTP/UDP Conversion to UMP

In some specific embodiments of the present invention, the NTPDase is an UTPase and/or a UDPase and assays that measure the enzymatic activity of the UTPase and/or UDPase activity of a cell following contacting, or exposure, or treatment of the cell with a candidate chemical substance that has an irritant potential are contemplated. In other embodiments, the chemical substance has the ability to modulate an UTPDase-mediated immune response, such as a hyperactive immune response. The UTPase activity is the ability to hydrolyse uridine triphosphate (UTP) into uridine diphosphate (UDP) and inorganic phosphate, or into uridine monophosphate (UMP) and pyrophosphate. The UDPase activity is the ability to hydrolyse UDP into UMP and inorganic phosphate. These are described by the following reactions:

$$UTP + H_2O \rightarrow UDP + P_i$$

$$UTP + H_2O \rightarrow UDP + P_1$$

One can use chromatographic or enzymatic or even immunological methods, such as those listed above, to detect the UTPase and UDPase activities.

VII. Transgenic Animals

In one embodiment of the invention, non-human transgenic animals are produced which contain a marker gene under the control of a CD39 promoter. Transgenic animals expressing this marker transgene, recombinant cell lines derived from such animals and transgenic embryos may be useful in methods for screening for and identifying agents that modulate expression of CD39. Transgenic animals of the present invention also can be used as models for studying responses to inflammatory agents.

In one embodiment of the invention, a CD39 promoter-marker transgene construct is introduced into a non-human host to produce a transgenic animal expressing a human, murine or other CD39 gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al.

1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

It also may be desirable to replace the endogenous CD39 by homologous recombination between the marker transgene construct and the endogenous CD39 gene. Alternatively, the endogenous gene may be eliminated by deletion as in the preparation of "knock-out" animals. Typically, a CD39 gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish.

VIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Role of CD39 in Chemical Inflammation

Materials and Methods

Animals and cell lines. Construction and initial characterization of $CD39^{-/-}$ and $CD39^{+/-}$ are described in Enjyoji et al., (1999), incorporated herein by reference. Three age- and sex-matched panels, i.e., $CD39^{-/-}$, $CD39^{+/-}$, and $CD39^{+/+}$ mice, were compared in parallel in all experiments. Phenotypic and functional properties of the XS52, XS106, 7–17, and Pam 212 lines have been reported previously (Xu et al., 1995; Matsue et al., 1999; Matsue et al., 1993).

Whole mount epidermal staining for LC and DETC. Epidermal sheets were separated from ear skin and footpad skin by ammonium thiocyanate treatment and subjected to immunofluorescence staining with FITC-conjugated mAb against IA, DEC205, or Vγ3 T cell receptor. The number of positive cells were counted by a third experimenter under a fluorescence microscope equipped with a digital camera and an image analysis software as before (Mummert et al., 2000, incorporated herein by reference). Epidermal sheets separated from footpad skin by EDTA treatment were examined for ecto-NTPDase activities with ATP and ADP substrates using standard protocols (Chaker et al., 1984).

Measurement of inflammatory skin responses. Mice received a single topical application of various irritant chemicals or vehicle alone on ear skin or single dorsal exposure to 1,500 $J/m^2$ of UV radiation (unfiltered FS20 sunlamps) and the ear thickness was measured by a third experimenter blinded to sample identity using an engineer's micrometer (Matsue et al., 1999; Matsue et al., 1993; Mummert et al., 2000). In some experiments, apyrase grade VII (0.2U/ear, Sigma, St. Louis, Mo.) was injected subcutaneously into the ear 10 min before and 1 hr after croton oil painting (Enjyoji et al., 1999). Allergic contact hypersensitivity responses were induced by sensitization with 1.25% OX, followed by challenge with 0.5% OX (Matsue et al., 1999; Mummert et al., 2000).

Results

CD39, originally identified as an activation marker expressed on B cells, T-cells, natural killer cells, DC, and endothelial cells (Maliszewski et al., 1994; Kansas et al., 1991) is now defined to be responsible for ecto-NTPDase activities on endothelial cells (Kaczmarek et al., 1996; Wang and Guidotti, 1996). Many ecto-NTPDases have since been isolated and cloned from different cell types and tissues, forming a rapidly growing family of ecto-NTPDases. Members of this family now include CD39, CD39L1 through L4, Golgi-associated ecto-ATPase and ecto-uridine diphosphatase (UDPase), lysosomal ecto-apyrase LALP70 and its variants, hepatic canalicular ecto-apyrase, and perhaps α-sarcoglycan (a component of the sarcoglycan complex of dystrophin-associated proteins). Taking the advantage of CD39-deficient mice (Enjyoji et al., 1999), the present inventors sought to determine whether CD39 is responsible for LC-associated ecto-NTPDase activities.

$CD39^{-/-}$ mice were indistinguishable from wild-type mice or heterozygous mice in terms of the number, distribution, or morphology of epidermal LC defined by the surface expression of IA and DEC205 (FIG. 1A and FIG. 1B). Likewise, $CD39^{-/-}$ mice contained normal networks of dendritic epidermal T-cells (DETC), which are skin resident γδ T-cells expressing a monoclonal T cell receptor containing the Vγ3 and Vδ1 determinants.

As reported by many investigators, epidermal LC in wild-type mice exhibited prominent ecto-NTPDase activities to hydrolyze both ATP and ADP substrates (FIG. 1C). In marked contrast, however, ecto-NTPDase activities were significantly diminished in $CD39^{+/-}$ LC, and virtually undetectable in $CD39^{-/-}$ LC, indicating that CD39 accounts for both ecto-ATPase and ecto-ADPase activities on LC. Keratinocytes are known express a modest ecto-ATPase activity visualized as a noise in the surface ATPase staining method (Chaker et al., 1984). A substantial noise was still detectable in $CD39^{-/-}$ mouse epidermis, suggesting that keratinocytes express other members of the ecto-NTPDase family.

Figure 2:
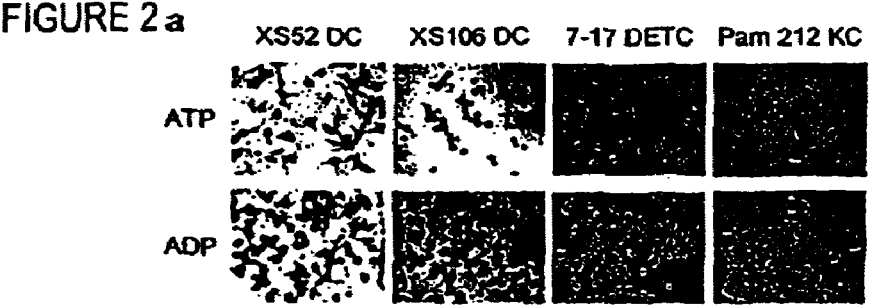
FIGS. 2A, 2B, 2C, & 2D. CD39 mRNA and protein expression by LC.
Figure 2:
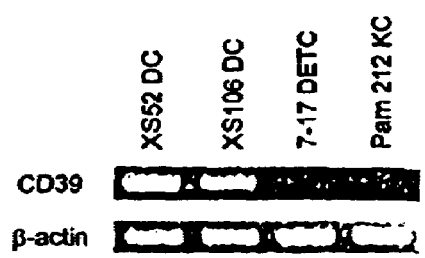
Figure 2:
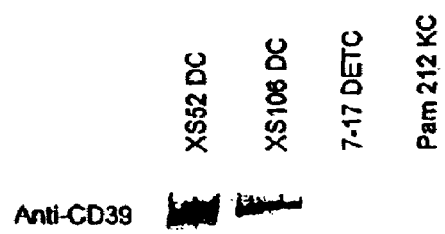
Figure 2:
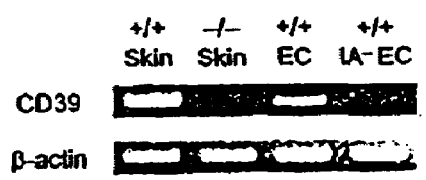

Stable LC lines, XS52 and XS106, established from newborn mouse skin, both hydrolyzed ATP and ADP substrates efficiently (FIG. 2A). By contrast, no apparent NTPDase activities were observed for 7–17 DETC line or Pam 212 keratinocyte line. CD39 mRNA expression was detected by RT-PCR in XS52 and XS106 LC lines, but not in 7–17 DETC or Pam 212 keratinocyte line. Likewise, membrane fractions prepared from XS52 and XS106 cells showed an apparent immunoreactive band of about 78 kD with anti-CD39 antibodies, whereas no immunoreactivity was observed in other epidermal cell lines (FIG. 2C). Finally, CD39 PCR signals were amplified from wild-type mouse skin, but not from $CD39^{-/-}$ mouse skin, and the PCR signals detected in wild-type mouse epidermis were abrogated by deletion of the $IA^+$ population (i.e., epidermal LC) (FIG. 2D). Thus, CD39 expression is relatively restricted to LC in mouse epidermis, further supporting the inventors hypothesis that CD39 alone is responsible for LC-associated ecto-NTPDase activities.

Figure 3A:
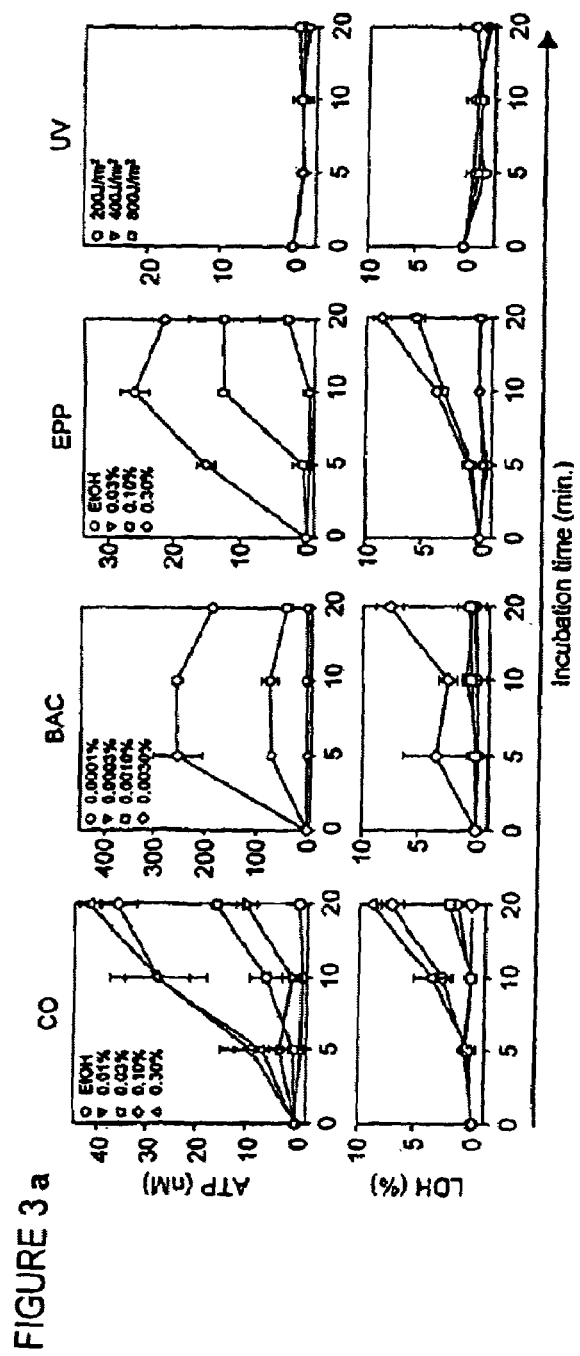
FIGS. 3A, 3B, & 3C. Release of ATP and ADP from Pam 212 keratinocytes following in vitro treatment with skin irritant chemicals.
Figure 3:
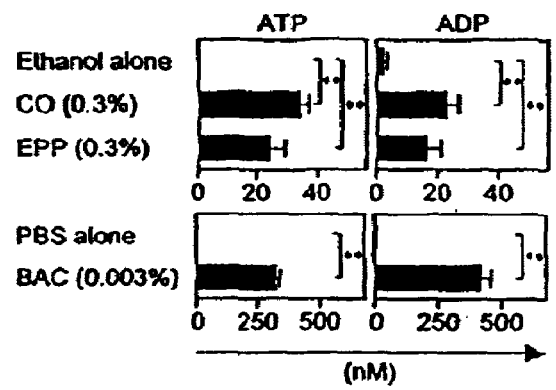
Figure 3:
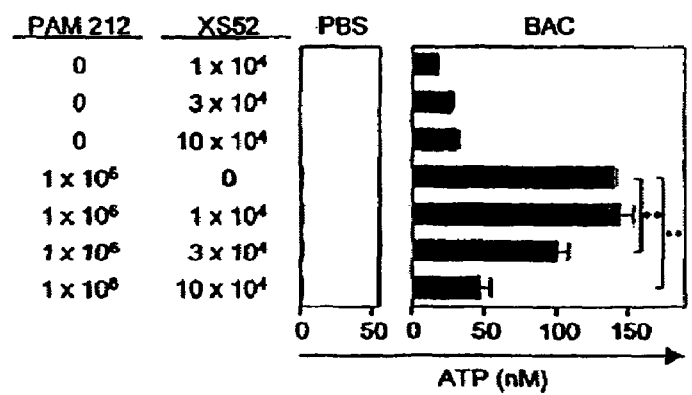

ATP and ADP released by endothelial cells and platelets are known to act as pro-inflammatory mediators in the vascular system. Therefore, the inventors further contemplated that, 1) keratinocytes may release ATP and/or ADP upon environmental insults and, if so, 2) LC-associated CD39 may play a protective role within the epidermal compartment by hydrolyzing otherwise pro-inflammatory mediators. To test the second hypothesis, the inventors examined ATP release from Pam 212 keratinocytes after treatment with three structurally diverse, skin-irritant chemicals, croton oil (CO), benzalkonium chloride (BAC), and ethyl phenylpropiolate (EPP). Exposure to each of these compounds triggered rapid ATP release in a time- and dose-dependent manner, with significant release observed within 5–10 min (upper panels in FIG. 3A). On the other hand, the inventors failed to detect significant ATP release after exposure to ultraviolet B (UVB) radiation. ATP was released as a consequence of plasma membrane disruption because the same three chemicals, but not UVB irradiation, caused rapid release of lactate dehydrogenase (LDH) as well (lower panels in FIG. 3A). ATP and ADP were detected at comparable levels in culture supernatants after treatment with each irritant chemical (FIG. 3B). These results demonstrate the potential of keratinocytes to release ATP and ADP in response to selected forms of environmental stimuli.

Figure 4:
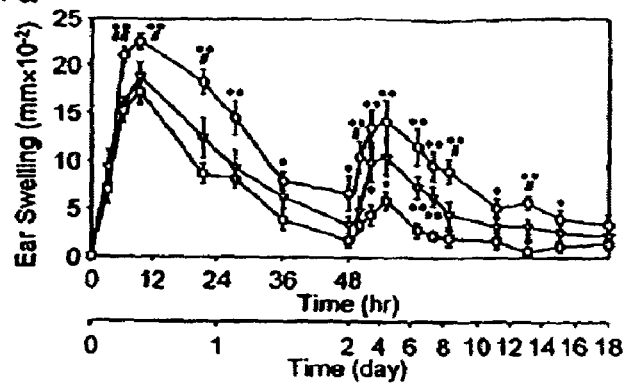
FIGS. 4A, 4B, 4C, 4D, 4E, 4F, 4G, & 4H. Irritant contact hypersensitivity responses in CD39-deficient mice. $CD39^{-/-}$ mice (circles), $CD39^{+/-}$ mice (triangles) or $CD39^{+/+}$ mice (squares) received topical application of 1% croton oil (FIG. 4A), 10% BAC (FIG. 4B), or 30% EPP (FIG. 4C) on the right ear and vehicle alone on the left ear. The data shown are the mean±SEM (n=10) of the swelling responses (the right ear thickness minus the left ear thickness) at the indicated time points, being displayed in two different time scales. Statistical significant differences compared to the $CD39^{+/+}$ mice or to the $CD39^{+/-}$ mice are indicated by asterisks or sharps, respectively (*/# p<0.05 and **/## p<0.01; two-tailed Student's t test).
Figure 4:
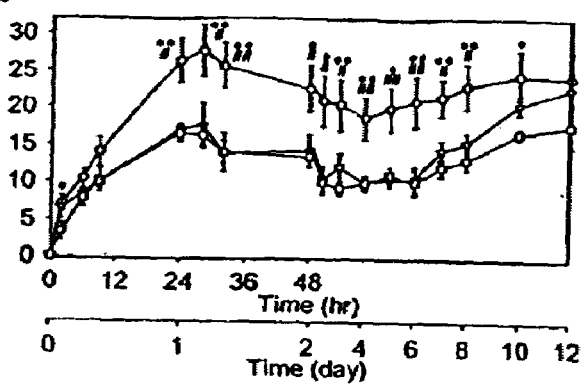
Figure 4:
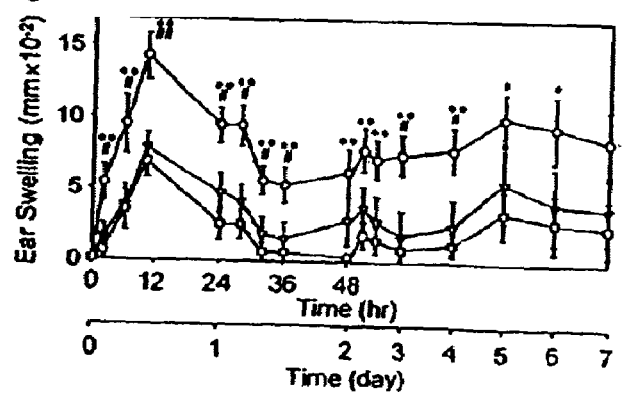
Figure 4:
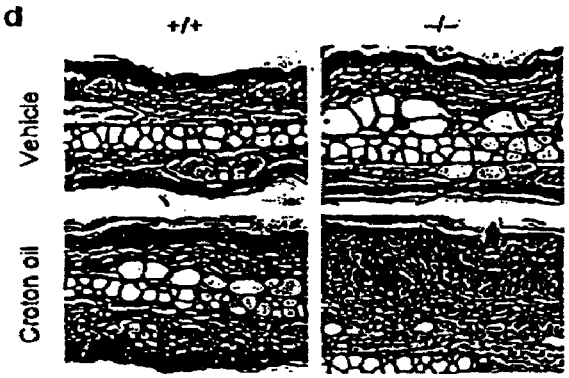
Figure 4:
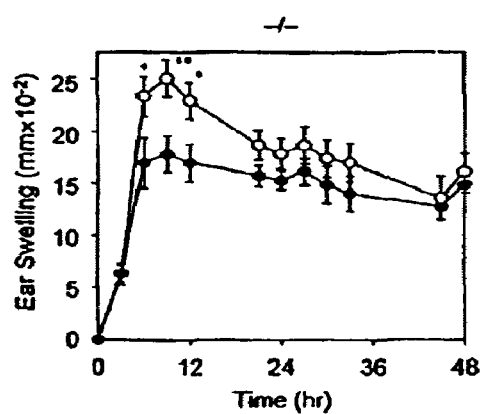
Figure 4:
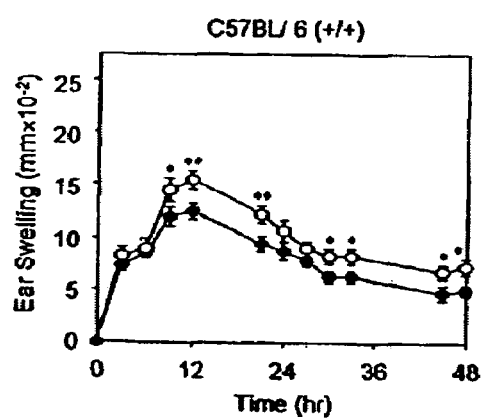
Figure 4:
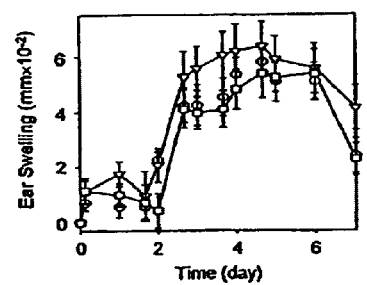
Figure 4:
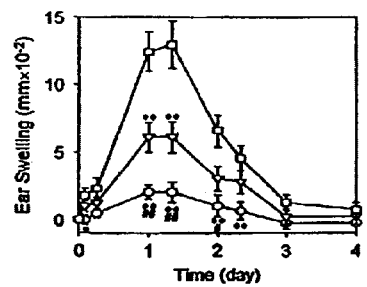

Addition of XS52 LC line (expressing CD39/NTPDase) to Pam 212 keratinocyte cultures reduced the levels of ATP detected in the media after BAC treatment, supporting the inventors hypothesis that extracellular nucleotides released by keratinocytes can be hydrolyzed by LC-associated CD39. To test this hypothesis in vivo, inflammatory responses among $CD39^{+/+}$, $CD39^{+/-}$, and $CD39^{-/-}$ mice to the above three chemicals were compared. $CD39^{-/-}$ mice showed significantly exacerbated ear swelling responses to CO than did $CD39^{+/+}$ mice in both early phase (6–48 hr) and late phase (2–15 days) (FIG. 4A). $CD39^{+/-}$ mice showed intermediate CO responses between the $CD39^{-/-}$ and $CD39^{+/+}$ groups. Ear swelling responses to two other chemicals (BAC and EPP) were also amplified significantly in $CD39^{-/-}$ mice than in $CD39^{+/+}$ mice (FIG. 4B and FIG. 4C). Intense late phase responses of $CD39^{-/-}$ mice to CO were characterized histologically by striking epidermal hyperplasia and marked leukocyte infiltration (FIG. 4D). Local injections of a soluble potato NTPDase (apyrase) immediately before and 1 hr after CO painting diminished the extent of early phase responses in $CD39^{-/-}$ mice, documenting that local deficiency in NTPDase activities was, in fact, responsible for the exacerbated inflammation (FIG. 4E). The same treatment further reduced the extent of CO-induced skin inflammation in the wild-type C57BL/6 mice, suggesting a causative role played by extracellular nucleotides in the development of irritant contact hypersensitivity responses (FIG. 4F).

$CD39^{-/-}$ mice and $CD39^{+/+}$ mice were comparable to each other in their acute inflammatory responses to UVB irradiation (FIG. 4G). Moreover, $CD39^{-/-}$ mice exhibited severe impairment in the development of T cell-mediated, allergic contact hypersensitivity to a reactive hapten, oxazolone (OX) (FIG. 4H). Thus, the present inventors results clearly indicate that CD39 deficiency does not simply amplify the extent of skin inflammation in a non-specific manner. Thus, CD39 expressed on LC (and on endothelial cells) plays a protective role against selected forms of environmental insults.

Over the last a few years, many ecto-NTPDases have been isolated and cloned from different cell types and tissues, forming a rapidly growing family of ecto-NTPDases. Members of this family now include CD39, CD39L1 through L4, Golgi-associated ecto-ATPase and ecto-uridine diphosphatase (UDPase), lysosomal ecto-apyrase LALP70 and its variants, hepatic canalicular ecto-apyrase, and perhaps α-sarcoglycan (a component of the sarcoglycan complex of dystrophin-associated proteins) (Chadwick et al., 1998; Zhong et al., 1999; Wang et al., 1998; Biederbick et al., 1999; Sevigny et al., 2000; Betto et al., 1999).

Three lines of evidence indicate that CD39 alone is responsible for LC-associated ecto-NTPDase activities. First, the present inventors observed CD39 mRNA expression by $IA^+$ epidermal cells in mouse skin, corroborating the previous immunofluorescence study describing CD39 expression by many cell types, including human LC (Kansas et al., 1991). Secondly, two LC-derived cell lines XS52 and XS106both expressed CD39 mRNA, CD39 protein, and ecto-NTPDase activities, whereas none of these features were detected in Pam 212 keratinocyte or 7–17 DETC line. Finally, ecto-NTPDase activities examined with either ATP or ADP substrate were significantly diminished in $CD39^{+/-}$ LC and virtually undetectable in $CD39^{-/-}$ LC, while surface expression of IA and DEC205 was not affected in $CD39^{+/-}$ LC or $CD39^{-/-}$ LC.

The inventors also observed that ATP and ADP were released rapidly from keratinocytes after treatment with skin irritant chemicals. Extracellularly released ATP and ADP are known to regulate intercellular communication via binding to various ligand gated ion channel P2X receptors and G-protein coupled P2Y receptors (Williams and Jarvis, 2000). For example, ATP and ADP that are released from endothelial cells by mechanical shear forces, stretch, changes in osmolarity, oxidative stress, and microbial products (e.g., lipopolysaccharides; LPS) exert apoptotic, inflammatory, and thrombotic effects in the vascular system. With respect to purinergic signaling in skin, in vitro treatment of keratinocytes with ATP has been reported to mobilize intracellular $Ca^{2+}$, inhibit terminal differentiation, affect proliferation, and induce apoptosis (Pillai and Bikle, 1992; Pillai et al., 1995; Sutter et al., 1991). In 1999, five groups reported independently that DC express mRNA for a variety of P2 receptors ($P2X_1$, $P2X_4$, $P2X_5$, $P2X_7$, $P2X_1$, $P2Y_1$, $P2Y_1$, $P2Y_2$, $P2Y_4$, $P2Y_5$, $P2Y_6$, $P2Y_{10}$, and $P2Y_{11}$) and that ATP triggers $Ca^{2+}$ influx, phenotypic maturation, chemotactic migration, and apoptosis of DC, whereas ADP (as well as UTP and UDP) induces production of IL-1β, IL-6, IL-10, and IL-12 (p40) by DC (Mutini et al., 1999; Liu et al., 1999; Coutinho-Silva et al., 1999; Berchtold et al., 1999; Marriott et al., 1999). Thus, nucleotides released by keratinocytes can potentially alter physiologically relevant functions of keratinocytes and LC. Thus, the present inventors have demonstrated a previously unrecognized role for LC, i.e., to regulate the magnitude of purinergic signaling in the skin via CD39-dependent hydrolysis of extracellularly released nucleotides.

Irritant contact dermatitis is the most common occupational health problem in the United States (Burnett et al., 1998). With regard to patho-physiology of this disease, secretion of pro-inflammatory cytokines, mainly IL-1 and TNFα, by chemically injured keratinocytes has been postulated as a causative mechanism (Effendy et al., 2000). The present inventors have demonstrated a new pathogenic mechanism as well as an intrinsic protective mechanism. To recapitulate the essence, the inventors observed: 1) Pam 212 keratinocytes released ATP and ADP rapidly after exposure to CO, BAC, or EPP; 2) $CD39^{-/-}$ mice exhibited exacerbated irritant contact dermatitis to the same chemicals, and 3) locally administered apyrase reduced the extent of acute inflammatory responses in $CD39^{-/-}$ mice. Ziganshina et al., (1996) have induced acute inflammation by local injection of ATP into the footpad, proving direct evidence for the skin inflammatory potential of ATP in vivo. In addition, the inventors have observed that $CD39^{-/-}$ mice exhibit markedly elevated inflammatory skin responses to locally administered ATP. Taken together, these observations illustrate a nucleotide-mediated pathogenic mechanism and a CD39-dependent protective mechanism for the development of irritant contact dermatitis.

The nucleotide theory of the present invention is in agreement, but not discordance, with the above cytokine theory because ATP and other nucleotides may act as mediators for cytokine secretion. For example, the inventors reported previously that LPS treatment triggers rapid ATP release and subsequent IL-1 secretion from endothelial cells and that LPS-induced IL-1 secretion can be inhibited by adenoviral delivery of CD39 cDNA to endothelial cells or by addition of soluble apyrase in the medium (Imai et al., 2000). Totally unexpected was the inventors finding that $CD39^{-/-}$ mice failed to mount full allergic contact hypersensitivity responses to OX. Studies are in progress in the inventors laboratories to define the functional role for CD39/NTPDase system in LC maturation and migration, LC-T cell interaction, and T cell activation and differentiation.

Example 2

Role of CD39 in Immune Responses

Materials and Methods

Measurement of DC function. The homing potential of LC was examined by counting the number of $IA^+$ epidermal cells 48 hr after local injection of recombinant TNFα (100 ng/animal) and the number of $FITC^+/IA^+$ cells in DLN 24 hr after topical application of 0.5% FITC (Mummert et al., 2000). Maturational states of migratory LC were assessed by the surface expression of CD86 and CD40 by the $FITC^+$ populations in DLN. In the in vitro reconstitution experiments, LN cells harvested 24 hr after OX painting were enriched for LC by centrifugation through 14.5% metrizamide and co-cultured with LN T-cells isolated from a different panel of mice that had received OX painting 7 days earlier. In adoptive transfer experiments, bone marrow-derived DC were pulsed with 1 mM TNBS in vitro and s.c. injected into $CD39^{+/+}$ mice ($5 \times 10^5$ $CD11C^+$ cells/animal); the recipient animals were challenged 7 days later with 1% TNCB (right ear) or vehicle alone (left ear) and examined for swelling responses.

Measurement of ATP responsiveness. ATP responsiveness of bone marrow-derived DC was examined by measuring: a) cell viabilities (7-AAD staining) after 60 min incubated with 2.5 mM ATP, b) IL-6 secretion (ELISA) after 16 hr incubation with 1 mM ATP, and c) uptake of LY (Molecular Probes, Eugene, Oreg.) after 15 min incubation with 3 mM ATP. Some samples were pre-treated for 10 min with apyrase (5 U/ml) or buffer alone before exposure to ATP.

Results

Functional role of CD39 in DC-induced T cell activation. Induction of allergic contact hypersensitivity requires several critical functions of LC, including: a) emigration of hapten-pulsed LC from the epidermal compartment, b) their subsequent migration to draining lymph nodes (DLN), c) maturation of migrating LC into fully potent DC, and d) DC-dependent activation of hapten-reactive T-cells. Therefore, the inventors sought to determine whether $CD39^{-/-}$ LC were unable to achieve one or more of the above tasks.

Figure 5:
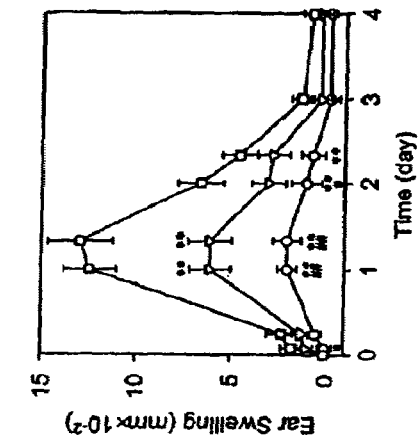
FIGS. 5A, 5B, 5C, 5D, 5E, 5F, 5G, & 5H. Attenuated immune responses in CD39-deficient mice. $CD39^{-/-}$ mice (circles), $CD39^{+/-}$ mice (triangles), or $CD39^{+/+}$ mice (squares) were examined for acute "sunburn" reactions (FIG. 5A) and for allergic contact hypersensitivity responses to OX (FIG. 5B). The data shown are the means±s.e.m. (n=10) of the swelling responses. Statistically significant differences compared to the $CD39^{+/+}$ panel or to the $CD39^{+/-}$ panel are indicated by asterisks or sharps, respectively (*/# P<0.05 and **/### P<0.01).
Figure 5:
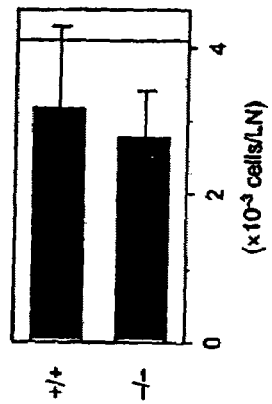
Figure 5:
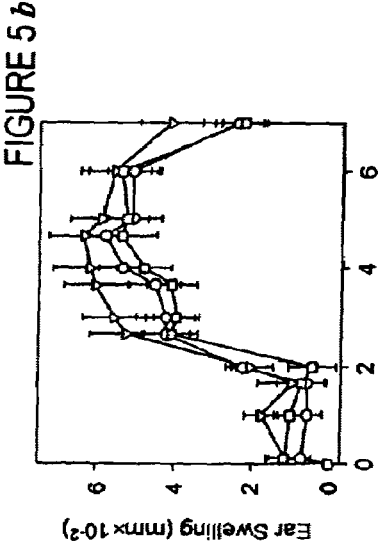
Figure 5:
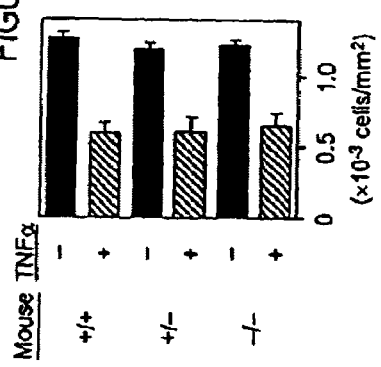

TNFα is known to mediate hapten-triggered LC migration (Cumberbatch and Kimber, 1995; Roake et aL., 1995). In fact, local injection of recombinant TNFα caused marked (about 50%) reduction in surface densities of $IA^+$ epidermal cells in $CD39^{+/+}$ mice (FIG. 5C). Importantly, $CD39^{-/-}$, $CD39^{+/-}$, and $CD39^{+/+}$ mice were comparable each other in the extent of LC emigration from epidermis. To test LC homing to DLN, FITC was topically applied as a reactive hapten to trigger LC migration and maturation and as a fluorescence probe to label epidermal cells. Therefore, the $FITC^+/IA^+$ cells recovered from the DLN represent the LC that have migrated from the FITC-painted sites (Love-Schimenti et al., 1994). $CD39^{-/-}$ mice were found to be comparable to $CD39^{+/+}$ mice in terms of the number of $FITC^+/IA^+$ cells recovered from DLN (FIG. 5D) as well as their preferential homing to the T cell area (FIG. 5E). Furthermore, $CD39^{-/-}$ mice were also indistinguishable from $CD39^{+/+}$ mice in terms of the maturational states of migratory LC as assessed by surface expression of CD86 and CD40 by $FITC^+$ LN cells (FIG. 5F). Thus, it appears that LC in $CD39^{-/-}$ mice are fully capable of migrating from epidermis to DLN and undergoing phenotypic maturation after hapten application.

The inventors next analyzed the antigen presenting potential of migratory LC in the in vitro reconstitution experiments, in which migratory LC harvested from DLN of OX-painted $CD39^{-/-}$ mice or $CD39^{+/+}$ mice were co-cultured with T-cells purified from OX-sensitized $CD39^{+/+}$ mice. Migratory LC from $CD39^{-/-}$ mice were found to be significantly less efficient than the wild-type counterpart in the in vitro ability to activate hapten-reactive T-cells (FIG. 5G). The observed difference between $CD39^{+/+}$ LC and $CD39^{-/-}$ LC was not as striking as that found originally in ear swelling responses to OX (FIG. 5B). This may be due to functional compensation by T cell-associated CD39 in the co-culture. These observations indicate functional impairment of antigen presenting capacity of $CD39^{-/-}$ LC.

The in vivo ability of $CD39^{-/-}$ LC to stimulate hapten-reactive T-cells in $CD39^{+/+}$ animals was also analyzed. Relatively large numbers of DC were expanded from the bone marrow of $CD39^{-/-}$ mice and $CD39^{+/+}$ mice; the resulting DC preparations in both panels contained >85% DC assessed by CD11c and IA expression and CD39 mRNA was detected by RT-PCR only in the $CD39^{+/+}$ panel. Adoptive transfer experiments were performed using these bone marrow-derived DC preparations. DC generated from $CD39^{-/-}$ mice and from $CD39^{+/+}$ mice were pulsed in vitro with trinitrobenzene sulfate (TNBS), and injected into $CD39^{+/+}$ recipient animals. Ear swelling responses measured after challenge with trinitrochlorobenzene (TNCB) were significantly lower in the mice sensitized with $CD39^{-/-}$ DC as compared to the positive control mice sensitized with $CD39^{+/+}$ DC (FIG. 5H). These results indicate that CD39 expression by DC is required for primary stimulation of hapten-reactive T-cells in living animals.

Figure 6A:
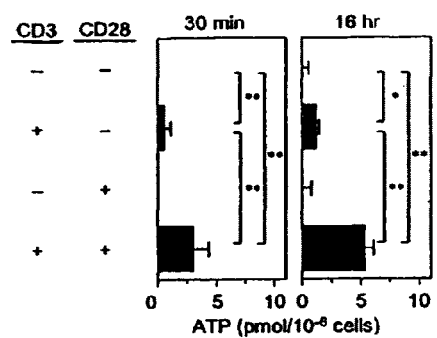
FIGS. 6A, 6B, & 6C. P2Y receptor desensitization in $CD39^{-/-}$ DC.
Figure 6B:
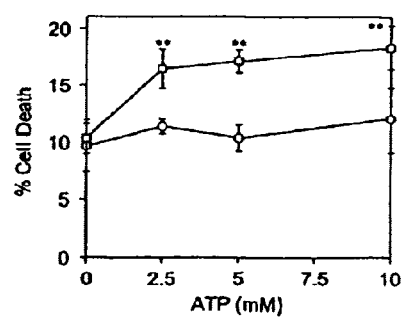
Figure 6C:
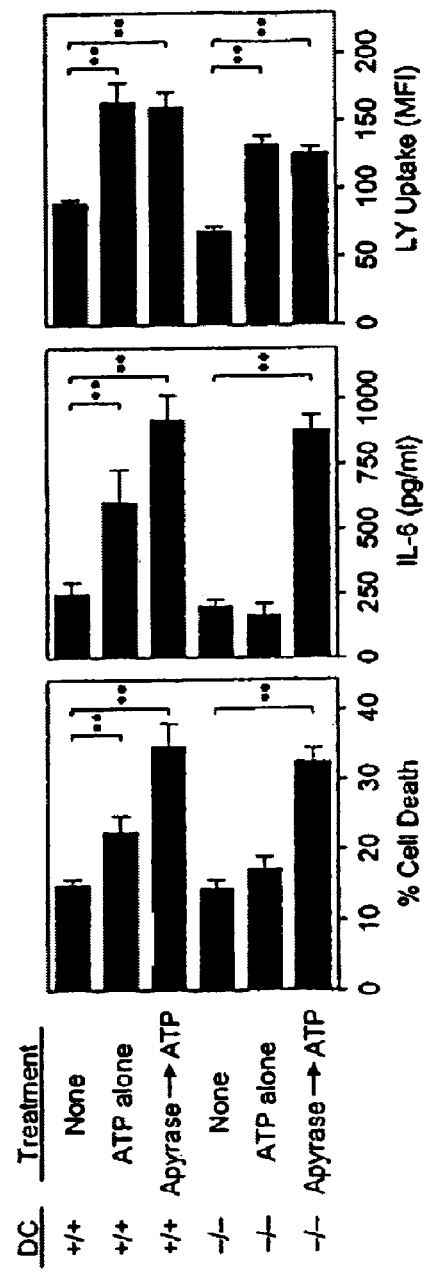

Unresponsiveness of $CD39^{-/-}$ DC to nucleotide signaling. Filippini et al. postulated that cytotoxic T-cells may utilize extracellular ATP to lyse target cells, based on the observations that T-cell-associated ATP levels increased after mitogenic stimulation and that their cytolytic capacity was inhibited partially by addition of soluble potato apyrase in the killing assay (Filippini et al., 1990). Stimulation of T-cells with immobilized anti-CD3 monoclonal antibodies (mAb) plus anti-CD28 mAb markedly elevated pericellular concentrations of ATP, whereas stimulation with anti-CD3 mAb alone induced only modest increases (FIG. 6A). Thus, it appears that T-cells, upon activation by DC, may provide substrates for DC-associated CD39 during antigen presentation. In this regard, DC are known to express several P2 receptors and to be highly susceptible to ATP-mediated cytolysis (DiVirgilio et al., 2001). Girolomoni et al. (1993), have proposed that ecto-ATPase activity on LC may play a protective role against ATP-induced death. Thus, T-cellassociated ATP may accelerate CD39$^{-/-}$ DC death during antigen presentation, thereby disabling them from delivering full T-cell activation signals. Unexpectedly, CD39$^{-/-}$ DC were found to be resistant to ATP-mediated cytolysis up to 10 mM ATP, whereas CD39$^{+/+}$ DC were killed significantly by 2.5 mM ATP (left panels in FIG. 6B). Furthermore, CD39$^{+/+}$ DC, but not CD39$^{-/-}$ DC, secreted IL-6 in response to stimulation with ATP (middle panels in FIG. 6C). Thus, CD39$^{-/-}$ DC were unresponsive, instead of hypersensitive, to ATP-mediated signaling.

Enjyoji et al., have previously observed that CD39$^{-/-}$ platelets fail to aggregate in response to nucleotide stimulation because of P2Y$_1$ receptor desensitization (Enjyoji et al., 1999). In fact, a brief exposure of CD39$^{-/-}$ DC to soluble apyrase restored their susceptibility to ATP-mediated cytolysis as well as their capacity to secrete IL-6 upon ATP stimulation (left and middle panels in FIG. 6C). Importantly, CD39$^{-/-}$ DC showed intact nucleotide responsiveness in terms of ATP-induced pore formation as assessed by lucifer yellow (LY) uptake (right panels in FIG. 6C). Thus, one or more P2Y receptors, but not ATP-gated ion channel P2X receptors, appear to be in the state of desensitization in CD39$^{-/-}$ DC. Taken all together, these results indicate a previously unrecognized role of DC-associated CD39 in regulating nucleotide-mediated intercellular communication between DC and T-cells during antigen presentation.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference:

U.S. Pat. No. 4,873,191

U.S. Pat. No. 5,252,479

U.S. Pat. No. 5,279,721

"Manipulating the mouse embryo," A Laboratory Manual, 2$^{nd}$ Ed., Hogan, Beddington, Costantimi, Long (Eds.), Cold Spring Harbor Laboratory Press, 1994.

Abeyama, K. et al. A role for NF-κB-dependent gene transactivation in sunburn. *J. Clin. Invest.* 105, 1751–1759 (2000).

Angel et al., "12-0-tetradecanoyl-phorbol-13-acetate Induction of the Human Collagenase Gene is Mediated by an Inducible Enhancer Element Located in the 5' Flanking Region," *Mol. Cell. Biol.,* 7:2256, 1987a.

Angel et al., "Phorbol Ester-Inducible Genes Contain a Common cis Element Recognized by a TPA-Modulated Trans-acting Factor," *Cell,* 49:729, 1987b.

Atchison and Perry, "Tandem Kappa Immunoglobulin Promoters are Equally Active in the Presence of the Kappa Enhancer: Implications for Model of Enhancer Function," *Cell,* 46:253, 1986.

Atchison and Perry, "The Role of the Kappa Enhancer and its Binding Factor NF-kappa B in the Developmental Regulation of Kappa Gene Transcription," *Cell,* 48:121, 1987.

Ausubel et al., In: *Current Protocols in Molecular Biology*, John, Wiley and Sons, Inc., 1994.

Baichwal and Sugden, "Vectors for gene transfer derived from animal DNA viruses: Transient and stable expression of transferred genes," In: Kucherlapati R, ed. Gene transfer. New York: Plenum Press, pp. 117–148, 1986.

Banchereau, J. et al. Immunobiology of dendritic cells. *Annu. Rev. Immunol.* 18, 767–811 (2000).

Banchereau, J. and Steinman, R. M. 1998. Dendritic cells and the control of immunity. *Nature* 392:245–252.

Banerji et al., "A lymphocyte-specific cellular enhancer is located downstream of the joining region in immunoglobulin heavy-chain genes," *Cell,* 35:729, 1983.

Banerji et al., "Expression of a Beta-Globin Gene is Enhanced by Remote SV40 DNA Sequences," *Cell,* 27:299, 1981.

Benvenisty and Neshif, *Proc. Nat'l Acad. Sci. USA* 83(24): 9551–9555, 1986.

Berchtold et al., "Human monocyte derived dendritic cells express functional P2X and P2Y receptors as well as ecto-nucleotidases," *FEBS Lett.,* 458:424–428, 1999.

Berkhout et al., "Tat trans-activates the human immunodeficiency virus through a nascent RNA target," *Cell,* 59:273, 1989.

Betto, R. et al. Ecto-ATPase activity of alpha-sarcoglycan (adhalin). *J. Biol. Chem.* 274, 7907–7912 (1999).

Biederbick, A., Rose, S. & Elsasser, H. P. A human intracellular apyrase-like protein, LALP70, localizes to lysosomal/autophagic vacuoles. *J. Cell Sci.* 112, 2473–2484 (1999).

Blanar et al., "A Gamma-Interferon-Induced Factor That Binds the Interferon Response Sequence of the MHC Class I Gene, H-2Kb," *EMBO J.,* 8:1139, 1989.

Bodine and Ley, "An Enhancer Element Lies 3' to the Human A Gamma Globin Gene," *EMBO J.,* 6:2997, 1987.

Boshart et al., "A very strong enhancer is located upstream of an immediate early gene of human cytomegalovirus," *Cell,* 41:521, 1985.

Bosze et al., "A transcriptional enhancer with specificity for erythroid cells is located in the long terminal repeat of the friend murine leukemia virus," *EMBO J.,* 5:1615, 1986.

Braddock et al., "HIV-I Tat Activates Presynthesized RNA I nthe Nucleus," *Cell,* 58:269, 1989.

Braun, Sevigny, Robson, Enjyoji, Guckelberger, Hammer, Di Virgilio, Zimmermann, "Assignment of ecto-nucleoside triphosphate diphosphohydrolase-1/cd39 expression to microglia and vasculature of the brain," *Eur J Neurosci*, (12):4357–4366, 2000.

Brinster, Chen, Trumbauer, Yagle, Palmiter, "Factors affecting the efficiency of introducing foreign DNA into mice by microinjecting eggs," *Proc Natl Acad Sci USA,* 82(13): 4438–4442, 1985.

Bulla and Siddiqui, "The hepatitis B virus enhancer modulates transcription of the hepatitis B virus surface-antigen gene from an internal location," *J. Virol.,* 62:1437, 1986.

Burnett, C. A., Lushniak, B. D., McCarthy, W. & Kaufman, J. Occupational dermatitis causing days away from work in U.S. private industry, 1993. *Am. J. Ind. Med.* 34, 568–573 (1998).

Campbell and Villarreal, "Functional analysis of the individual enhancer core sequences of polyoma virus: Cell-specific uncoupling of DNA replication from transcription," *Mol. Cell. Biol.*, 8:1993, 1988.

Campere and Tilghman, "Postnatal repression of the α-fetoprotein gene is enhancer independent," *Genes and Dev.*, 3:537, 1989.

Campo, Spandidos, Lang, Wilkie, "Transcriptional control signals in the genome of bovine papilloma virus type 1," *Nature*, 303:77, 1983.

Celander and Haseltine, "Glucocorticoid regulation of murine leukemia virus transcription elements is specified by determinants within the viral enhancer region," *J. Virology*, 61:269, 1987.

Celander et al., "Regulatory elements within the murine leukemia virus enhancer regions mediate glucocorticoid responsiveness," *J. Virology*, 62:1314, 1988.

Chadwick and Frischauf, "The CD39-like gene family: identification of three new human members (CD39L2, CD39L3, and CD39L4), their murine homologues, and a member of the gene family from Drosophila melanogaster," *Genomics*, 50:357–367, 1998.

Chaker, Tharp, Bergstresser, "Rodent epidermal Langerhans cells demonstrate greater histochemical specificity for ADP than for ATP and AMP," *J. Invest Dermatol.*, 82:496–500, 1984.

Chandler et al., "DNA sequences bound specifically by glucocorticoid receptor in vitro render a heterlogous promoter hormone responsive in vivo," *Cell*, 33:489, 1983.

Chang et al., "Glucose-regulated Protein (GRP94 and GRP78) Genes Share Common Regulatory Domains and are Coordinately Regulated by Common Trans-acting Factors," *Mol. Cell. Biol.*, 9:2153, 1989.

Chattedjee et al., "Negative Regulation of the Thyroid-Stimulating Hormone Alpha Gene by Thyroid Hormone: Receptor Interaction Adjacent to the TATA Box," *Proc. Natl. Acad. Sci. U.S.A.*, 86:9114, 1989.

Choi et al., "An Altered Pattern of Cross-Resistance in Multi-Drug-Resistant Human Cells Results From Spontaneous Mutations in the Mdr-1 (P-glycoprotein) Gene," *Cell*, 53:519, 1988.

Coffin, "Retroviridae and their replication," In: *Virology*, Fields et al. (eds.), New York: Raven Press, pp. 1437–1500, 1990.

Cohen et al., "A Repetitive Sequence Element 3' of the Human c-Ha-ras1 Gene Has Enhancer Activity,"*J. Cell. Physiol.*, 5:75, 1987.

Costa et al., "The cell-specific enhancer of the mouse transthyretin (prealbumin) gene binds a common factor at one site and a liver-specific factor(s) at two other sites," *Mol. Cell. Biol.*, 8:81, 1988.

Couch et al., *Am. Rev. Resp. Dis.*, 88:394–403, 1963.

Coupar et al., "A general method for the construction of recombinant vaccinia virus expressing multiple foreign genes," *Gene*, 68:1–10, 1988.

Coutinho-Silva et al., "P2Z/P2X7 receptor-dependent apoptosis of dendritic cells," *Am. J. Physiol.* 276: C1139–C1147, 1999.

Coutinho-Silva, R. et al. P2Z/P2X7 receptor-dependent apoptosis of dendritic cells. *Am. J. Physiol.* 276, C1139–C1147 (1999).

Cripe et al., "Transcriptional Regulation of the Human Papilloma Virus-16 E6–E7 Promoter by a Keratinocyte-Dependent Enhancer, and by Viral E2 Trans-Activator and Repressor Gene Products: Implications for Cervical Carcinogenesis," *EMBO J.*, 6:3745, 1987.

Culotta and Hamer, "Fine Mapping of a Mouse Metallothionein Gene Metal-Response Element," *Mol. Cell. Biol.*, 9:1376, 1989.

Cumberbatch, M. & Kimber, I. Tumour necrosis factor-α is required for accumulation of dendritic cells in draining lymph nodes and for optimal contact sensitization. *Immunology* 84, 31–35 (1995).

Dandolo et al., "Regulation of Polyma Virus Transcription in Murine Embryonal Carcinoma Cells," *J. Virology*, 47:55, 1983.

De Villiers et al., "Polyoma Virus DNA Replication Requires an Enhancer," *Nature*, 312:242, 1984.

Deschamps et al., "Identification of a Transcriptional Enhancer Element Upstream From the Proto-Oncogene Fos," *Science*, 230:1174, 1985.

Di Virgillo, F. et al. Nucleotide receptors: an emerging family of regulatory molecules in blood cells. *Blood* 97, 587–600 (2001).

Dubensky et al., *Proc. Nat'l Acad. Sci. USA*, 81:7529–7533, 1984.

Dumbrowski et al., Ecto-ATPase: an activation marker necessary for effector cell function, *Immunol Rev.*, February; 161:111–8, 1998.

Edbrooke et al., "Identification of cis-Acting Sequences Responsible for Phorbol Ester Induction of Human Serum Amyloid A Gene Expression Via a Nuclear-Factor-κB-like Transcription Factor," *Mol. Cell. Biol.*, 9:1908, 1989.

Edlund et al., "Cell-Specific Expression of the Rat Insulin Gene: Evidence for Role of Two Distinct 5' Flanking Elements," *Science*, 230:912, 1985.

Effendy, I., Loffler, H. & Maibach, H. I. Epidermal cytokines in murine cutaneous irritant responses. *J. Appl. Toxicol.* 20, 335–341 (2000).

Effendy, I., Loffler, H., and Maibach, H. I. 2000. Epidermal cytokines in murine cutaneous irritant responses. *J. Appl. Toxicol.* 20:335–341.

Enjyoji, et al. "Targeted disruption of cd39/ATP diphosphohydrolase results in disordered hemostasis and thromboregulation," *Nat. Med.*, 5:1010–1017, 1999.

EPO 0273085

Fechheimer et al., "Transfection of mammalian cells with plasmid DNA by scrape loading and sonication loading," *Proc. Natl. Acad. Sci. USA* 84:8463–8467, 1987

Feng and Holland, "HIV-I Tat Trans-Activation Requires the Loop Sequence Within Tar," *Nature*, 334:6178, 1988.

Ferkol et al., *FASEB J.*, 7:1081–1091, 1993.

Ferrari, D. et al. The P2 purinergic receptors of human dendritic cells: identification and coupling to cytokine release. *FASEB J.* 14, 2466–2476 (2000).

Filippini, A., Taffs, R. E. & Sitkovsky, M. V. Extracellular ATP in T-lymphocyte activation: possible role in effector functions. *Proc. Natl. Acad. Sci. U.S.A* 87, 8267–8271 (1990).

Firak and Subramanian, "Minimal Transcription Enhancer of Simian Virus 40 is a 74-Base-Pair Sequence that Has Interacting Domains," *Mol. Cell. Biol.*, 6:3667, 1986.

Foecking and Hofstetter, "Powerful and Versatile Enhancer-Promoter Unit for Mammalian Expression Vectors," *Gene*, 45:101, 1986.

Friedmann, "Progress toward human gene therapy," *Science*, 244:1275–1281, 1989.

Fujita et al., "Interferon-Beta Gene Regulation: Tandemly Repeated Sequences of a Synthetic 6-bp Oligomer Function as a Virus-Inducible Enhancer," *Cell*, 49:357, 1987.

Gayle, R. B., III et al. Inhibition of platelet function by recombinant soluble ecto-ADPase/CD39. *J. Clin. Invest.* 101, 1851–1859 (1998).

Ghosh and Bachhawat, "Targeting of liposomes to hepatocytes," In: Wu G. and C. Wu ed. Liver diseases, targeted diagnosis and therapy using specific receptors and ligands. New York: Marcel Dekker, pp. 87–104, 1991.

Ghosh-Choudhury et al., "Protein IX, a minor component of the human adenovirus capsid, is essential for the packaging of full-length genomes," *EMBO J.*, 6:1733–1739, 1987.

Gilles et al., "A Tissue-Specific Transcription Enhancer Element is Lcoated in the Major Intron of a Rearranged Immunoglobulin Heavy-Chain Gene," *Cell*, 33:717, 1983.

Girolomoni et al., "Epidermal Langerhans cells are resistant to the permeabilizing effects of extracellular ATP: in vitro evidence supporting a protective role of membrane ATPase, " *J. Invest Dermatol.*, 100:282–287, 1993.

Gloss et al., "The Upstream Regulatory Region of the Human Papilloma Virus-16 Contains an E2 Protein-Independent Enhancer Which is Specific for Cervical Carcinoma Cells and Regulated by Glucocorticoid Hormones," *EMBO J.*, 6:3735, 1987.

Godbout et al., "Fine-Structure Mapping of the Three Mouse Alpha-Fetoprotein Gene Enhancers," *Mol. Cell. Biol.*, 8:1169, 1988.

Gomez-Foix et al., "Adenovirus-mediated transfer of the muscle glycogen phosphorylase gene into hepatocytes confers altered regulation of glycogen," *J. Biol. Chem.*, 267:25129–25134, 1992.

Goodbourn and Maniatis, "Overlapping Positive and Negative Regulatory Domains of the Human β-Interferon Gene," *Proc. Natl. Acad. Sci. USA*, 85:1447, 1988.

Goodboum et al., "The Human Beta-Interferon Gene Enhancer is Under Negative Control," *Cell*, 45:601, 1986.

Gopal, "Gene transfer method for transient gene expression, stable transformation, and cotransformation of suspension cell cultures," *Mol. Cell. Biol.* 5:1188–1190, 1985.

Grabbe, S. & Schwarz, T. Immunoregulatory mechanisms involved in elicitation of allergic contact hypersensitivity. *Immunol. Today* 19, 37–44 (1998).

Graham and Prevec, "Manipulation of adenovirus vectors," In: *Gene Transfer and Expression Protocols*, Murray, E. J., ed., Humana, New Jersey, vol. 7, 109–128, 1991.

Graham et al., "Characteristics of a human cell line transformed by DNA from human adenovirus type 5", *J. Gen. Virol.*, 36:59–72, 1977.

Greene et al., "HIV-1, and Normal T-Cell Growth: Transcriptional Strategies and Surprises," *Immunology Today*, 10:272, 1989.

Grosschedl and Baltimore, "Cell-Type Specificity of Immunoglobulin Gene Expression is Regulated by at Least Three DNA Sequence Elements," *Cell*, 41:885, 1985.

Grunhaus and Horwitz, "Adenovirus as cloning vector," *Seminar in Virology*, 3:237–252, 1992.

Harland and Weintraub, "Translation of mRNA injected into *Xenopus* oocytes is specifically inhibited by antisense RNA," *J. Cell Biol.* 101:1094–1099, 1985.

Haslinger and Karin, "Upstream Promoter Element of the Human Metallothionein-II Gene Can Act Like an Enhancer Element," *Proc. Natl. Acad. Sci. U.S.A.*, 82:8572, 1985.

Hauber and Cullen, "Mutational Analysis of the Trans-Activation-Responsive Region of the Human Immunodeficiency Virus Type I Long Terminal Repeat," *J. Virology*, 62:673, 1988.

Heine, et al., Functional characterization of rat ecto-ATPase and ecto-ATP diphosphohydrolase after heterologous expression in CHO cells, *Eur J Biochem.* May; 262(1): 102–7, 1999.

Hen et al., "A Mutated Polyoma Virus Enhancer Which is Active in Undifferentiated Embryonal Carcinoma Cells is not Repressed by Adenovirus-2 E1A Products," *Nature*, 321:249, 1986.

Hensel et al., "PMA-Responsive 5' Flanking Sequences of the Human TNF Gene," *Lymphokine Res.*, 8:347, 1989.

Hermonat and Muzyczka, "Use of adeno-associated virus as a mammalian DNA cloning vector; transduction of neomycin resistance into mammalian tissue culture cells," *Proc. Nat'l. Acad. Sci. USA*, 81:6466–6470, 1984.

Herr and Clarke, "The SV40 Enhancer is Composed of Multiple Functional Elements That Can Compensate for One Another," *Cell*, 45:461, 1986.

Hersdorffer et al., "Efficient gene transfer in live mice using a unique retroviral packaging line," *DNA Cell Biol.*, 9:713–723, 1990.

Herz and Gerard, *Proc. Nat'l Acad. Sci. USA*, 90:2812–2816, 1993.

Hirochika et al., "Enhancers and Trans-Acting E2 Transcriptional Factors of Papilloma Viruses," *J. Virol.*, 61:2599, 1987.

Hirsch et al., "Identification of Positive and Negative Regulatory Elements Governing Cell-Type-Specific Expression of the Neural-Cell-Adhesion-Molecule Gene," *Mol. Cell. Biol.*, 10:1959, 1990.

Holbrook et al., "cis-Acting Transcriptional Regulatory Sequences in the Gibbon Ape Leukemia Virus (GALV) Long Terminal Repeat," *Virology*, 157:211, 1987.

Horlick and Benfield, "The Upstream Muscle-Specific Enhancer of the Rat Muscle Creatine Kinase Gene is Composed of Multiple Elements," *Mol. Cell. Biol.*, 9:2396, 1989.

Horwich et al. "Synthesis of hepadenovirus particles that contain replication-defective duck hepatitis B virus genomes in cultured HuH7 cells," *J. Virol.*, 64:642–650, 1990.

Huang et al., "Glucocorticoid Regulation of the Ha-MuSV p21 Gene Conferred by Sequences From Mouse Mammary Tumor Virus," *Cell*, 27:245, 1981.

Hug et al., "Organization of the Murine Mx Gene and Characterization of its Interferon- and Virus-Inducible Promoter," *Mol. Cell. Biol.*, 8:3065, 1988.

Hwang et al., "Characterization of the S-Phase-Specific Transcription Regulatory Elements in a DNA-Replication-Independent Testis-Specific H2B (TH2B) Histone Gene," *Mol. Cell. Biol.*, 10:585, 1990.

Imagawa et al., "Transcription Factor AP-2 Mediates Induction by Two Different Signal-Transduction Pathways: Protein Kinase C and cAMP," *Cell*, 51:251, 1987.

Imai, M., Goepfert, C., Kaczmarek, E. & Robson, S. C. CD39 modulates IL-1 release from activated endothelial cells. *Biochem. Biophys. Res. Commun.* 270, 272–278 (2000).

Imbra and Karin, "Phorbol Ester Induces the Transcriptional Stimulatory Activity of the SV40 Enhancer," *Nature*, 323:555, 1986.

Imler et al., "Negative Regulation Contributes to Tissue Specificity of the Immunoglobulin Heavy-Chain Enhancer," *Mol. Cell. Biol.*, 7:2558, 1987.

Imperiale and Nevins, "Adenovirus 5 E2 Transcription Unit: an E1A-Inducible Promoter with an Essential Element that Functions Independently of Position or Orientation," *Mol. Cell. Biol.*, 4:875, 1984.

Inaba, K. et al. Generation of large numbers of dendritic cells from mouse bone marrow cultures supplemented with granulocyte/macrophage colony-stimulating factor. *J. Exp. Med.* 176, 1693–1702 (1992).

Jakobovits et al., "A Discrete Element 3' of Human Immunodeficiency Virus 1 (HIV-1) and HIV-2 mRNA Initiation Sites Mediates Transcriptional Activation by an HIV Trans-Activator," *Mol. Cell. Biol.*, 8:2555, 1988.

Jameel and Siddiqui, "The Human Hepatitis B Virus Enhancer Requires Transacting Cellular Factor(s) for Activity," *Mol. Cell. Biol.*, 6:710, 1986.

Jaynes et al., "The Muscle Creatine Kinase Gene is Regulated by Multiple Upstream Elements, Including a Muscle-Specific Enhancer," *Mol. Cell. Biol.*, 8:62, 1988.

Jiang, Lozanski, Samols, Kushner, "Induction of human serum amyloid A in Hep 3B cells by IL-6 and IL-1 beta involves both transcriptional and post-transcriptional mechanisms, " *J Immunol*, 54(2):825–831, 1995.

Johnson et al., "Muscle Creatine Kinase Sequence Elements Regulating Skeletal and Cardiac Muscle Expression in Transgenic Mice," *Mol. Cell. Biol.*, 9:3393, 1989.

Jones and Shenk, "Isolation of deletion and substitution mutants of adenovirus type 5," *Cell*, 13:181–188, 1978.

Kaczmarek et al., "Identification and characterization of CD39/vascular ATP diphosphohydrolase," *J. Biol. Chem.*, 271:33116–33122, 1996.

Kadesch and Berg, "Effects of the Position of the Simian Virus 40 Enhancer on Expression of Multiple Transcription Units in a Single Plasmid," *Mol. Cell. Biol.*, 6:2593, 1986.

Kaneda et al., "Increased expression of DNA cointroduced with nuclear protein in adult rat liver," *Science*, 243: 375–378, 1989.

Kansas, Wood, Tedder, "Expression, distribution, and biochemistry of human CD39. Role in activation-associated homotypic adhesion of lymphocytes," *J. Immunol.*, 146: 2235–2244, 1991.

Karin et al., "Metal-Responsive Elements Act as Positive Modulators of Human Metallothionein-IIA Enhancer Activity," *Mol. Cell. Biol.*, 7:606, 1987.

Karlsson et al., *EMBO J.*, 5:2377–2385, 1986.

Katinka et al., "Expression of Polyoma Early Functions in Mouse Embryonal Carcinoma Cells Depends on Sequence Rearrangements in the Beginning of the Late Region," *Cell*, 20:393, 1980.

Katinka et al., "Polyoma DNA Sequences Involved in the Control of Viral Gene Expression in Murine Embryonal Carcinoma Cells," *Nature*, 290:720, 1981.

Kato et al., "Expression of hepatitis β virus surface antigen in adult rat liver," *J. Biol. Chem.*, 266:3361–3364, 1991.

Kawamoto et al., "Identification of the Human Beta-Actin Enhancer and its Binding Factor," *Mol. Cell. Biol.*, 8:267, 1988.

Khakh, B. S. Molecular physiology of P2X receptors and ATP signalling at synapses. *Nature Rev. Neurosci.* 2, 165–174 (2001).

Kiledjian et al., "Identification and Characterization of Two Functional Domains Within the Murine Heavy-Chain Enhancer," *Mol. Cell. Biol.*, 8:145, 1988.

Klamut et al., "Molecular and Functional Analysis of the Muscle-Specific Promoter Region of the Duchenne Muscular Dystrophy Gene," *Mol. Cell. Biol.*, 10:193, 1990.

Knowles et al., Inhibition of an ecto-ATP-diphosphohydrolase by azide, *Eur J Biochem.*, June; 262(2):349–57, 1999.

Koch et al., "Anatomy of a New B-Cell-Specific Enhancer," *Mol. Cell. Biol.*, 9:303, 1989.

Kriegler et al., "A Novel Form of TNF/Cachectin Is a Cell-Surface Cytotoxix Transmembrane Protein: Ramifications for the Complex Physiology of TNF," *Cell*, 53:45, 1988.

Kriegler et al., "Promoter Substitution and Enhancer Augmentation Increases the Penetrance of the SV40 A Gene to Levels Comparable to That of the Harvey Murine Sarcoma Virus Ras Gene in Morphologic Transformation," In: *Gene Expression*, eds. D. Hamer and M. Rosenberg. New York: Alan R. Liss, 1983.

Kriegler et al., "Transformation Mediated by the SV40 T Antigens: Separation of the Overlapping SV40 Early Genes with a Retroviral Vector," *Cell*, 38:483, 1984a.

Kriegler et al., "Viral Integration and Early Gene Expression Both Affect the Efficiency of SV40 Transformation of Murine Cells: Biochemical and Biological Characterization of an SV40 Retrovirus," In: *Cancer Cells 2/Oncogenes and Viral Genes*, Van de Woude et al. eds, Cold Spring Harbor: Cold Spring Harbor Laboratory, 1984b.

Ku and Mortensen, "The mouse C-reactive protein (CRP) gene is expressed in response to IL-1 but not IL-6," *Cytokine*, 5(4):319–326, 1993.

Kuhl et al., "Reversible Silencing of Enhancers by Sequences Derived From the Human IFN-alpha Promoter," *Cell*, 50:1057, 1987.

Kunz et al., "Identification of the Promoter Sequences Involved in the Interleukin-6-Dependant Expression of the Rat Alpha-2-Macroglobulin Gene," *Nucl. Acids Res.*, 17:1121, 1989.

Larsen et al., "Repression Medaites Cell-Type-Specific Expression of the Rat Growth Hormone Gene," *Proc. Natl. Acad. Sci. U.S.A.*, 83:8283, 1986.

Laspia et al., "HIV-1 Tat Protein Increases Transcriptional Initiation and Stabilizes Elongation," *Cell*, 59:283, 1989.

Latimer et al., "Highly Conserved Upstream Regions of the $\alpha_1$-Antitrypsin Gene in Two Mouse Species Govern Liver-Specific Expression by Different Mechanisms," *Mol. Cell. Biol.*, 10:760,1990.

Laughlin et al., "Latent Infection of KB Cells with Adeno-Associated Virus Type 2," *J. Virol.*, 60:515–524, 1986.

Le Gal La Salle et al., *Science*, 259:988–990, 1993.

Lebkowski et al., "Adeno-associated virus: a vector system for efficient introduction and integration of DNA into a variety of mammalian cell types," *Mol. Cell. Biol.*, 8:3988–3996, 1988.

Lee et al., "Glucocorticoids Regulate Expression of Dihydrofolate Reductase cDNA in Mouse Mammary Tumor Virus Chimaeric Plasmids," *Nature*, 294:228, 1981.

Levinson et al., "Activation of SV40 Genome by 72-Base-Pair Tandem Repeats of Moloney Sarcoma Virus," *Nature*, 295:79, 1982.

Levrero et al., "Defective and nondefective adenovirus vectors for expressing foreign genes in vitro and in vivo," *Gene*, 101:195–202, 1991.

Lin et al., "Delineation of an Enhancerlike Positive Regulatory Element in the Interleukin-2 Receptor α-Chain Gene," *Mol. Cell. Biol.*, 10:850, 1990.

Liu et al. "Expression and a role of functionally coupled P2Y receptors in human dendritic cells," *FEBS Lett.*, 445: 402–408, 1999.

Love-Schimenti, C. D. & Kripke, M. L. Dendritic epidermal T-cells inhibit T cell proliferation and may induce tolerance by cytotoxicity. *J. Immunol.* 153, 3450–3456 (1994).

Lundin, "Optimised assay of firefly luciferase with stable light emission. In: Bioluminescence and Chemiluminescence," Szalay, Kricka, Stanley, (Eds.), John Wiley and Sons, Chichester, 291–295, 1993.

Luria et al., "Promoter Ehancer Elements in the Rearranged Alpha-Chain Gene of the Human T-Cell Receptor," *EMBO J.*, 6:3307, 1987.

Lusky and Botchan, "Transient Replication of Bovine Papilloma Virus Type 1 Plasmids: cis and trans Requirements," *Proc. Natl. Acad. Sci. U.S.A.*, 83:3609, 1986.

Lust W D, Feussner G K, Barbehenn E K, Passonneau J V, "The enzymatic measurement of adenine nucleotides and P-creatine in picomole amounts," *Anal Biochem*, January 15;110(2):258–66 1981.

Majors and Varmus, "A Small Region of the Mouse Mammary Tumor Virus Long Terminal Repeat Confers Glucocorticoid Hormone Regulation on a Linked Heterologous Gene," *Proc. Natl. Acad. Sci. U.S.A.*, 80:5866, 1983.

Maliszewski et al., "The CD39 lymphoid cell activation antigen. Molecular cloning and structural characterization," *J. Immunol.*, 153:3574–3583, 1994.

Maliszewski, C. R. et al. The CD39 lymphoid cell activation antigen. Molecular cloning and structural characterization. *J. Immunol.* 153, 3574–3583 (1994).

Mann et al., "Construction of a retrovirus packaging mutant and its use to produce helper-free defective retrovirus," *Cell*, 33:153–159, 1983.

Marcus, A. J. et al. The endothelial cell ecto-ADPase responsible for inhibition of platelet function is CD39. *J. Clin. Invest.* 99, 1351–1360 (1997).

Markowitz et al., "A safe packaging line for gene transfer: Separating viral genes on two different plasmids," *J. Virol.*, 62:1120–1124, 1988.

Marriott, Inscho, Bost, "Extracellular uridine nucleotides initiate cytokine production by murine dendritic cells," *Cell. Immunol.*, 195:147–156, 1999.

Matsue et al., "Induction of antigen-specific immunosuppressive by CD95L cDNA-transfected 'killer' dendritic cells," *Nature Med.*, 5:930–937, 1999.

Matsue, Bergstresser, Takashima, "Keratinocyte-derived IL-7 serves as a growth factor for dendritic epidermal T-cells in mice," *J. Immunol.*, 151:6012–6019, 1993.

Matsue, H. et al. Induction of antigen-specific immunosuppression by CD95L cDNA-transfected "killer" dendritic cells. *Nature Med.* 5, 930–937 (1999).

Matsue, H., Bergstresser, P. R. & Takashima, A. Keratinocyte-derived IL-7 serves as a growth factor for dendritic epidermal T-cells in mice. *J. Immunol.* 151, 6012–6019 (1993).

McNeall et al., "Hyperinducible Gene Expression From a Metallotionein Promoter Containing Additional Metal-Responsive Elements," *Gene*, 76:81, 1989.

Miksicek et al., "Glucocorticoid Responsiveness of the Transcriptional Enhancer of Moloney Murine Sarcoma Virus," *Cell*, 46:203, 1986.

Mordacq and Linzer, "Co-localization of Elements Required for Phorbol Ester Stimulation and Glucocorticoid Repression of Proliferin Gene Expression," *Genes and Dev.*, 3:760, 1989.

Moreau et al., "The SV40 Base-Repair Repeat Has a Striking Effect on Gene Expression Both in SV40 and Other Chimeric Recombinants," *Nucl. Acids Res.*, 9:6047, 1981.

Mulligan, *Science*, 260:926–932, 1993.

Mummert, Mohamadzadeh, Mummert, Mizumoto, Takashima, "Development of a peptide inhibitor or hyaluronan-mediated leukocyte trafficking," *J. Exp. Med.*, 192:769–779, 2000.

Musesing et al., "Regulation of mRNA Accumulation by a Human Immunodeficiency Virus Trans-Activator Protein," *Cell*, 48:691, 1987.

Mutini et al., "Mouse dendritic cells express the $P2X_7$ purinergic receptor: characterization and possible participation in antigen presentation," *J. Immunol.*, 163:1958–1965, 1999.

Ng et al., "Regulation of the Human Beta-Actin Promoter by Upstream and Intron Domains," *Nuc. Acids Res.*, 17:601, 1989.

Nicolas and Rubinstein, "Retroviral vectors," In: *Vectors: A survey of molecular cloning vectors and their uses*, Rodriguez and Denhardt (eds.), Stoneham: Butterworth, pp. 494–513, 1988.

Nicolau et al., "Liposomes as carriers for in vivo gene transfer and expression," *Methods Enzymol.*, 149:157–176, 1987.

Nihei, O. K., de Carvalho, A. C., Savino, W. & Alves, L. A. Pharmacologic properties of $P_{2Z}/P2X_7$ receptor characterized in murine dendritic cells: role on the induction of apoptosis. *Blood* 96, 996–1005 (2000).

Ondek et al., "Discrete Elements Within the SV40 Enhancer Region Display Different Cell-Specific Enhancer Activities," *EMBO J.*, 6:1017, 1987.

Ornitz et al., "Promoter and Enhancer Elements From the Rat Elastase I Gene Function Independently of Each Other and of Heterologous Enhancers," *Mol. Cell. Biol.*, 7:3466, 1987.

Palmiter et al., "Differential Regulation of Metallothionein-Thymidine Kinase Fusion Genes in Transgenic Mice and Their Offspring," *Cell*, 29:701, 1982.

Paskind et al., *Virology*, 67:242–248, 1975.

Pech et al., "Functional Identification of Regulatory Elements Within the Promoter Region of Platelet-Derived Growth Factor 2," *Mol. Cell. Biol.*, 9:396, 1989.

Pelletier and Sonenberg, "Internal initiation of translation of eukaryotic mRNA directed by a sequence derived from poliovirus RNA," *Nature*, 334:320–325, 1988.

Perales, Ferkol, Beegen, Ratnoff, Hanson, "Gene transfer in vivo: sustained expression and regulation of genes introduced into the liver by receptor-targeted uptake," *Proc. Natl. Acad. Sci. USA*, 91(9):4086–4090, 1994.

Perez-Stable and Constantini, "Roles of Fetal γ-globin Promoter Elements and the Adult β-globin 3' Enhancer in the Stage-Specific Expression of Globin Genes," *Mol. Cell. Biol.*, 10:1116, 1990.

Picard and Schaffner, "A lymphocyte-specific enhancer in the mouse immunoglobulin kappa gene," *Nature*, 307:83, 1984.

Pillai and Bikle, "Adenosine triphosphate stimulates phosphoinositide metabolism, mobilizes intracellular calcium, and inhibits terminal differentiation of human epidermal keratinocytes," *J. Clin. Invest*, 90:42–51, 1992.

Pillai, Bikle, Su, Ratnam, Abe, "1,25-Dihydroxyvitamin D3 upregulates the phosphatidylinositol signaling pathway in human keratinocytes by increasing phospholipase C levels," *J. Clin. Invest*, 96:602–609, 1995.

Pinkert et al., "An albumin enhancer located 10 kb upstream functions along with its promoter to direct efficient, liver-specific expression in transgenic mice," *Genes and Dev.*, 1:268, 1987.

Plesner, L. Ecto-ATPases: identities and functions. *Int. Rev. Cytol.* 158, 141–214 (1995).

Ponta et al., "Hormonal response region in the mouse mammary tumor virus long terminal repeat can be dissociated from the proviral pomoter and has enhancer properties," *Proc. Natl. Acad. Sci. U.S.A.*, 82:1020, 1985.

Porton et al., "Immunoglobulin Heavy-Chain Enhancer is Required to Maintain Transfected γ2A Gene Expression in a pre-B-cell Line," *Mol. Cell. Biol.*, 10:1076, 1990.

Potter et al., "Enhancer-dependent expression of human k immunoglobulin genes introduced into mouse pre-B lymphocytes by electroporation," *Proc. Natl Acad. Sci. USA*, 81:7161–7165, 1984.

Queen and Baltimore, "Immunoglobulin Gene Transcription is Activated by Downstream Sequence Elements," *Cell*, 35:741, 1983.

Quinn et al., "Multiple Components are Required for Sequence Recognition of the AP1 Site in the Gibbon Ape Leukemia Virus Enhancer," *Mol. Cell. Biol.*, 9:4713, 1989.

Racher et al., *Biotechnology Techniques*, 9:169–174, 1995.

Ragot et al., *Nature*, 361:647–650, 1993.

Ralevic et al., Receptors for purines and pyrimidines, *Pharmacol Rev.*, September; 50(3):413–92, 1998.

Ralevic, V. & Burnstock, G. Receptors for purines and pyrimidines. *Pharmacol. Rev.* 50, 413–492 (1998).

Redondo et al., "A T-Cell-Specific Transcriptional Enhancer Within the Human T-Cell Receptor δ Locus," *Science*, 247:1225, 1990.

Reisman and Rotter, "Induced Expression From the Moloney Murine Leukemia Virus Long Terminal Repeat During Differentiation of Human Myeloid Cells is Mediated Through its Transcriptional Enhancer," *Mol. Cell. Biol.*, 9:3571, 1989.

Remington's Pharmaceutical Sciences, 15th Edition, Chapter 61, pages 1035–1038 and 1570–1580.

Renan, "Cancer genes: current status, future prospects, and applicants in radiotherapy/oncology," *Radiother. Oncol.*, 19:197–218, 1990.

Resendez Jr. et al., "Identification of Highly Conserved Regulatory Domains and Protein-Binding Sites in the Promoters of the Rat and Human Genes Encoding the Stress-Inducible 78-kilodalton Glucose-Regulated Protein," *Mol. Cell. Biol.*, 8:4579, 1988.

Ridgeway, "Mammalian expression vectors," In: *Vectors: A survey of molecular cloning vectors and their uses*. Rodriguez and Denhardt, eds. Stoneham: Butterworth, pp. 467–492, 1988.

Ripe et al., "Regulatory Elements in the 5' Flanking Region and the First Intron Contribute to Transcriptional Control of the Mouse alpha-1-type Collagen Gene," *Mol. Cell. Biol.*, 9:2224, 1989.

Rittling et al., "AP-1/jun-binding Sites Mediate Serum Inducibility of the Human Vimentin Promoter," *Nuc. Acids Res.*, 17:1619, 1989.

Roake, J A. et al. Dendritic cell loss from nonlymphoid tissues after systemic administration of lipopolysaccharide, tumor necrosis factor, and interleukin 1. *J. Exp. Med.* 181, 2237–2247 (1995).

Rosen et al., "The Location of cis-acting Regulatory Sequences in the Human T-Cell Lymphotropic Virus Type III (HTLV-111/LAV) Long Terminal Repeat," *Cell*, 41:813, 1988.

Rosenfeld et al., *Cell*, 68:143–155, 1992.

Rosenfeld et al., *Science*, 252:431–434, 1991.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acad. Sci. USA*, 86:9079–9083, 1989.

Sakai, Helms, Carlstedt-Duke, Gustafsson, Rottman, and Yamamoto, "Hormone-Mediated Repression: A Negative Glucocorticoid-Response Element From the Bovine Prolactin Gene," *Genes and Dev.*, 2:1144, 1988.

Sambrook, Fritsch, Maniatis, *Molecular Cloning: A Laboratory Manual*, 2nd Ed., Cold Spring Harbor Press, Cold Spring Harbor, N.Y., 1989.

Samulski et al., *J. Virol.*, 61(10):3096–3101, 1987.

Satake et al., "Biological Activities of Oligonucleotides Spanning the F9 Point Mutation Within the Enhancer Region of Polyoma Virus DNA," *J. Virology*, 62:970, 1988.

Schaffner et al., "Redundancy of Information in Enhancers as a Principle of Mammalian Transcription Control," *J. Mol. Biol.*, 201:81, 1988.

Searle et al., "Building a Metal-Responsive Promoter With Synthetic Regulatory Elements," *Mol. Cell. Biol.*, 5:1480, 1985.

Sellers, L. A. et al. Adenosine nucleotides acting at the human P2Y1 receptor stimulate mitogen-activated protein kinases and induce apoptosis. *J. Biol. Chem.* 276, 16379–16390 (2001).

Sevigny, J. et al. Identification and characterization of a novel hepatic canalicular ATP diphosphohydrolase. *J. Biol. Chem.* 275, 5640–5647 (2000).

Sharp and Marciniak, "HIV Tar: an RNA Enhancer?," *Cell*, 59:229, 1989.

Shaul and Ben-Levy, "Multiple nuclear proteins in liver cells are bound to hepatitis B virus enhancer element and its upstream sequences," *EMBO J*, 6(7):1913–1920, 1987.

Sherman et al., "Class II Box Consensus Sequences in the HLA-DRα Gene: Transcriptional Function and Interaction with Nuclear Proteins," *Mol. Cell. Biol.*, 9:50, 1989.

Sleigh and Lockett, "SV40 Enhancer Activation During Retinoic-Acid-Induced Differentiation of F9 Embryonal Carcinoma Cells," *J. EMBO*, 4:3831, 1985.

Spalholz et al., "Transactivation of a Bovine Papilloma Virus Transcriptional Regulatory Element by the E2 Gene Product," *Cell*, 42:183, 1985.

Spandau and Lee, "Trans-Activation of Viral Enhancers by the Hepatitis B Virus X Protein," *J. Virology*, 62:427, 1988.

Spandidos and Wilkie, "Host-Specificities of Papilloma Virus, Moloney Murine Sarcoma Virus and Simian Virus 40 Enhancer Sequences," *EMBO J.*, 2:1193, 1983.

Stephens and Hentschel, "The Bovine Papilloma Virus Genome and its Uses as a Eukaryotic Vector," *Biochem. J.*, 248:1, 1987.

Stratford-Perricaudet and Perricaudet, In: *Human Gene Transfer*, O. Cohen-Haguenauer et al., eds., John Libbey Eurotext, France, 51–61, 1991.

Stratford-Perricaudet et al, *Hum. Gene. Ther.*, 1:241–256, 1990.

Stuart et al., "Identification of Multiple Metal Regulatory Elements in Mouse Metallothionein-I Promoter by Assaying Synthetic Sequences," *Nature*, 317:828, 1985.

Sullivan and Peterlin, "Transcriptional Enhancers in the HLA-DQ Subregion," *Mol. Cell. Biol.*, 7:3315, 1987.

Suter, Crameri, Slattery, Millard, Gonzalez, "Extracellular ATP and some of its analogs induce transient rises in cytosolic free calcium in individual canine keratinocytes, *J. Invest Dermatol.*, 97:223–229, 1991.

Swartzendruber and Lehman, "Neoplastic Differentiation: Interaction of Simian Virus 40 and Polyoma Virus with Murine Teratocarcinoma Cells," *J. Cell. Physiology*, 85:179, 1975.

Takebe et al., "SRα Promoter: An Efficient and Versatile Mammalian cDNA Expression System Composed of the Simian Virus 40 Early Promoter and the R-U5 Segment of Human T-Cell Leukemia Virus Type 1 Long Terminal Repeat," *Mol. Cell. Biol.*, 8:466, 1988.

Tavernier et al., "Deletion Mapping of the Inducible Promoter of Human IFN-beta Gene," *Nature,* 301:634, 1983.

Taylor and Kingston, "Ela Trans-Activation of Human HSP70 Gene Promoter Substitution Mutants is Independent of the Composition of Upstream and TATA Elements," *Mol. Cell. Biol.,* 10:176, 1990b.

Taylor and Kingston, "Factor Substitution in a Human HSP70 Gene Promoter: TATA-Dependent and TATA-Independent Interactions," *Mol. Cell. Biol.,* 10:165, 1990a.

Taylor et al., "Stimulation of the Human Heat-Shock Protein 70 Promoter in vitro by Simian Virus 40 Large T Antigen," *J. Biol. Chem.,* 264:15160, 1989.

Temin, "Retrovirus vectors for gene transfer: Efficient integration into and expression of exogenous DNA in vertebrate cell genome," *In: Gene Transfer,* Kucherlapati (ed.), New York: Plenum Press, pp. 149–188, 1986.

Thiesen et al., "A DNA Element Responsible for the Different Tissue Specificities of Friend and Moloney Retroviral Enhancers," *J. Virology,* 62:614, 1988.

Top et. al., *J. Infect. Dis.,* 124:155–160, 1971.

Treisman, "Transient Accumulation of c-fos RNA Following Serum Stimulation Requires a Conserved 5' Element and c-fos 3' Sequences," *Cell,* 42:889, 1985.

Tronche et al., "Anatomy of the Rat Albumin Promoter," *Mol. Biol. Med.,* 7:173, 1990.

Tronche et al., "The Rat Albumin Promoter: Cooperation with Upstream Elements is Required When Binding of APF/HNF 1 to the Proximal Element is Partially Impaired by Mutation or Bacterial Methylation," *Mol. Cell. Biol.,* 9:4759, 1989.

Trudel and Constantini, "A 3' Enhancer Contributes to the Stage-Specific Expression of the Human Beta-Globin Gene," *Genes and Dev.,* 6:954, 1987.

Tur-Kaspa et al., "Use of electroporation to introduce biologically active foreign genes into primary rat hepatocytes," *Mol. Cell Biol.,* 6:716–718, 1986.

Tyndall et al., "A Region of the Polyoma Virus Genome Between the Replication Origin and Late Protein-Coding Sequences is Required in cis for Both Early Gene Expression and Viral DNA Replication," *Nuc. Acids. Res.,* 9:6231, 1981.

Vannice and Levinson, "Properties of the Human Hepatitis B Virus Enhancer: Position Effects and Cell-Type Non-specificity," *J. Virology,* 62:1305, 1988.

Varmus et al., *Cell,* 25:23–36, 1981.

Vasseur et al., "Isolation and Characterization of Polyoma Virus Mutants Able to Develop in Multipotential Murine Embryonal Carcinoma Cells," *Proc. Natl. Acad. Sci. U.S.A.,* 77:1068, 1980.

von Kugelgen I & Wetter A, Molecular pharmacology of P2Y-receptors, *Naunyn Schmiedebergs Arch Pharmacol,* November; 362(4–5): 310–23, 2000.

Wagner et al., *Science,* 260:1510–1513, 1990.

Wang and Guidotti, "CD39 is an ecto-(Ca2+,Mg2+)-apyrase," *J. Biol. Chem.,* 271:9898–9901, 1996.

Wang et al., *Biochimica et Biophysica Acta* 888(2):225–36, 1986.

Wang, T. F. & Guidotti, G. CD39 is an ecto-(Ca2+, Mg2+)-apyrase. *J. Biol. Chem.* 271, 9898–9901 (1996).

Wang, T. F. & Guidotti, G. Golgi localization and functional expression of human uridine diphosphatase. *J. Biol. Chem.* 273, 11392–11399 (1998).

Warny, M. et al. P2Y(6) nucleotide receptor mediates monocyte interleukin-8 production in response to UDP or lipopolysaccharide. *J. Biol. Chem.* 276, 26051–26056 (2001).

Weber et al., "An SV40 'Enhancer Trap' Incorporates Exogenous Enhancers or Generates Enhancers From its Own Sequences," *Cell,* 36:983, 1984.

Weinberger et al. "Localization of a Repressive Sequence Contributing to B-cell Specificity in the Immunoglobulin Heavy-Chain Enhancer," *Mol. Cell. Biol.,* 8:988, 1984.

Williams and Jarvis, "Purinergic and pyrimidinergic receptors as potential drug targets," *Biochem. Pharmacol.,* 59:1173–1185, 2000.

Williams et al., Purinergic and pyrimidinergic receptors as potential drug targets, *Biochem Pharmacol.,* May 15; 59(10):1173–85, 2000.

Winoto and Baltimore, "αβ-lineage-specific Expression of the α T-Cell Receptor Gene by Nearby Silencers," *Cell,* 59:649, 1989.

Wolff and Winkelmann, "Ultrastructural localization of nucleoside triphosphatase in Langerhans cells," *J. Invest Dermatol.,* 48:50–54, 1967.

Wong et al., "Appearance of β-lactamase activity in animal cells upon liposome mediated gene transfer," *Gene,* 10:87–94, 1980.

Wu and Wu, "Receptor-mediated in vitro gene transfections by a soluble DNA carrier system," *J. Biol. Chem.,* 262: 4429–4432, 1987.

Wu and Wu, *Adv. Drug Delivery Rev.,* 12:159–167, 1993.

Wu and Wu, *Biochemistry,* 27:887–892, 1988.

Xu, S. et al., "Successive generation of antigen-presenting, dendritic cell lines from murine epidermis," *J. Immunol.,* 154:2697–2705, 1995.

Yeung, Mulero, McGowan, Bajwa, Ford, "CD39L2, a gene encoding a human nucleoside diphosphatase, predominantly expressed in the heart," *Biochemistry,* 39(42): 12916–12923, 2000.

Yutzey et al. "An Internal Regulatory Element Controls Troponin I Gene Expression," *Mol. Cell. Biol.,* 9:1397, 1989.

Zhong, X. and Guidotti, G. A yeast Golgi E-type ATPase with an unusual membrane topology. *J. Biol. Chem.* 274:32704–32711, 1999.

Ziganshina, L. E., Ziganshin, A. U., Hoyle, C. H. & Bumstock, G. Acute paw oedema formation induced by ATP: re-evaluation of the mechanisms involved. *Inflamm. Res.* 45, 96–102 (1996).

Zimmermann, H. 5'-Nucleotidase: molecular structure and functional aspects. *Biochem. J.* 285, 345–365 (1992).

Zinchuk et al., Ecto-ATPase activity in cerebellum: implication to the function of synaptic transmission, *Brain Res.* January 2; 815(1):111–5, 1999.

What is claimed is:

1. A method for predicting irritant potential of a candidate substance comprising:
   a) providing a mammalian keratinocyte cell that releases a ATP and/or ADP in response to an inflammatory agent;
   b) culturing said mammalian keratinocyte cell with a candidate substance; and
   c) determining ATP and/or ADP release from said mammalian keratinocyte cell,
   wherein an increase in ATP and/or ADP release from said mammalian keratinocyte cell, as compared to ATP and/or ADP release in the absence of said candidate substance, indicates that said candidate substance is an irritant.

2. The method of claim 1, wherein said cell is a human keratinocyte.

3. The method of claim 1, wherein said cell is a mouse keratinocyte.

4. The method of claim 3, wherein said cell is a PAM 212 cell.

5. The method of claim 1, wherein determining ATP and/or ADP release from said cell comprises measuring nucleotide concentration in the cell culture medium.

6. The method of claim 5, wherein measuring ATP and/or ADP concentration compnses an enzymatic assay.

7. The method of claim 6, wherein said enzymatic assay is a luciferin-luciferase assay.

8. The method of claim 1, wherein said candidate substance is a naturally-occurring compound.

9. The method of claim 1, wherein said candidate substance is a man-made compound.

10. The method of claim 1, further comprising measuring ATP and/or ADP release from said cell in the absence of said candidate substance.

11. The method of claim 1, further comprising a control comprising:
   a) contacting said cell with a known irritant; and
   b) measuring ATP and/or ADP release from said cell.

* * * * *

UNITED STATES PATENT AND TRADEMARK OFFICE
CERTIFICATE OF CORRECTION

PATENT NO. : 7,067,254 B2
APPLICATION NO. : 10/074220
DATED : June 27, 2006
INVENTOR(S) : Kumamoto et al.

It is certified that error appears in the above-identified patent and that said Letters Patent is hereby corrected as shown below:

In claim 6, column 59, line 7, delete "compnses" and insert --comprises-- therefor.

Signed and Sealed this

Seventh Day of November, 2006

JON W. DUDAS
*Director of the United States Patent and Trademark Office*